(12) United States Patent
Fakhouri et al.

(10) Patent No.: US 11,363,998 B2
(45) Date of Patent: Jun. 21, 2022

(54) MANAGING AUDIO FOR REMOTE HEALTH SERVICES

(71) Applicant: Teladoc Health, Inc., Purchase, NY (US)

(72) Inventors: Tamer Fakhouri, Millbrae, CA (US); Amar Kendale, Sunnyvale, CA (US); Gene V. Kozin, San Jose, CA (US); Polina A. Segalova, Redwood City, CA (US); Keval Mehta, Dublin, CA (US)

(73) Assignee: Teladoc Health, Inc., Purchase, NY (US)

( * ) Notice: Subject to any disclaimer, the term of this patent is extended or adjusted under 35 U.S.C. 154(b) by 0 days.

(21) Appl. No.: 16/800,007

(22) Filed: Feb. 25, 2020

(65) Prior Publication Data

US 2020/0383571 A1    Dec. 10, 2020

Related U.S. Application Data

(63) Continuation of application No. PCT/US2020/015805, filed on Jan. 30, 2020.
(Continued)

(51) Int. Cl.
*G08B 1/08* (2006.01)
*A61B 5/00* (2006.01)
(Continued)

(52) U.S. Cl.
CPC .......... *A61B 5/7465* (2013.01); *A61B 5/0004* (2013.01); *A61B 5/0022* (2013.01);
(Continued)

(58) Field of Classification Search
None
See application file for complete search history.

(56) References Cited

U.S. PATENT DOCUMENTS 6,542,846 B1    4/2003    Miller et al.
7,935,307 B2    5/2011    Angelides
(Continued)

FOREIGN PATENT DOCUMENTS

CA    2 999 150 A1    3/2017
JP    6025599 B2    11/2016
(Continued)

OTHER PUBLICATIONS

U.S. Appl. No. 16/799,978, filed Feb. 25, 2020, Boulos, et al.
(Continued)

*Primary Examiner* — Julie B Lieu

(57) ABSTRACT

A mobile health device includes a sensor that monitors values of a health metric of a person, a control component that controls the device to perform actions as part of providing a health service, and components of the device that receive the control signal and perform an action to provide the health service based on the control signal. The components include user output components for producing sound and/or displaying information and where providing the health service includes playing information as sound, displaying information as text, displaying information as motion video, and/or displaying information still images. The control component includes an input that receives audio signals corresponding to the monitored values of the health metric and produces a control signal based on information about the person, including the monitored values of the health metric of the person. The mobile health device may also include a network interface component.

19 Claims, 11 Drawing Sheets

Related U.S. Application Data

(60) Provisional application No. 62/865,411, filed on Jun. 24, 2019, provisional application No. 62/858,759, filed on Jun. 7, 2019.

(51) Int. Cl.

| | | |
|---|---|---|
| *A61B 5/145* | (2006.01) | |
| *G16H 10/60* | (2018.01) | |
| *G16H 40/67* | (2018.01) | |
| *G16H 50/30* | (2018.01) | |
| *A61B 5/021* | (2006.01) | |
| *G16H 20/00* | (2018.01) | |
| *G16H 70/20* | (2018.01) | |
| *G16H 80/00* | (2018.01) | |
| *G06N 20/00* | (2019.01) | |
| *G06N 5/04* | (2006.01) | |
| *G16H 40/63* | (2018.01) | |
| *G05B 15/02* | (2006.01) | |
| *G05D 23/19* | (2006.01) | |
| *G16H 30/20* | (2018.01) | |
| *G16H 50/20* | (2018.01) | |
| *G16H 30/40* | (2018.01) | |
| *G06T 7/00* | (2017.01) | |
| *G16H 15/00* | (2018.01) | |
| *G16H 50/70* | (2018.01) | |
| *G06F 1/26* | (2006.01) | |
| *G06F 9/54* | (2006.01) | |
| *G06F 21/33* | (2013.01) | |
| *G06F 1/3206* | (2019.01) | |
| *G06F 1/20* | (2006.01) | |

(52) U.S. Cl.
CPC .......... *A61B 5/021* (2013.01); *A61B 5/14532* (2013.01); *A61B 5/7405* (2013.01); *G05B 15/02* (2013.01); *G05D 23/1917* (2013.01); *G06F 1/26* (2013.01); *G06F 1/3206* (2013.01); *G06F 9/542* (2013.01); *G06F 21/33* (2013.01); *G06N 5/04* (2013.01); *G06N 20/00* (2019.01); *G06T 7/0002* (2013.01); *G16H 10/60* (2018.01); *G16H 15/00* (2018.01); *G16H 20/00* (2018.01); *G16H 30/20* (2018.01); *G16H 30/40* (2018.01); *G16H 40/63* (2018.01); *G16H 40/67* (2018.01); *G16H 50/20* (2018.01); *G16H 50/30* (2018.01); *G16H 50/70* (2018.01); *G16H 70/20* (2018.01); *G16H 80/00* (2018.01); *G06F 1/206* (2013.01); *G06T 2207/30168* (2013.01)

(56) References Cited

U.S. PATENT DOCUMENTS

| 8,066,640 | B2 | 11/2011 | Angelides |
| 8,568,309 | B2 | 10/2013 | Angelides |
| 8,812,244 | B2 | 8/2014 | Angelides |
| 8,967,855 | B1 | 3/2015 | Joshi et al. |
| 8,978,055 | B1* | 3/2015 | Sudo ............... H04N 21/44222 725/10 |
| 2004/0117210 | A1 | 6/2004 | Brown |
| 2005/0143671 | A1* | 6/2005 | Hastings ............... A61B 5/002 600/513 |
| 2005/0146431 | A1* | 7/2005 | Hastings ............ G08B 21/0294 340/539.12 |
| 2005/0148890 | A1* | 7/2005 | Hastings ............... A61B 5/411 600/509 |
| 2005/0151640 | A1* | 7/2005 | Hastings ............... G16H 40/67 340/539.11 |
| 2006/0184421 | A1 | 8/2006 | Lipsky et al. |
| 2006/0229502 | A1 | 10/2006 | Pollock et al. |
| 2008/0001735 | A1* | 1/2008 | Tran .................. G08B 21/0492 340/539.22 |
| 2008/0118184 | A1 | 5/2008 | Panabaker et al. |
| 2008/0221396 | A1 | 9/2008 | Garces et al. |
| 2013/0187780 | A1* | 7/2013 | Angelides ........... G06F 3/04817 340/573.1 |
| 2014/0122085 | A1* | 5/2014 | Piety ...................... G01M 7/00 704/275 |
| 2015/0164349 | A1 | 6/2015 | Gopalakrishnan et al. |
| 2015/0286784 | A1 | 10/2015 | Hagigi et al. |
| 2016/0139787 | A1 | 5/2016 | Joo et al. |
| 2016/0140834 | A1* | 5/2016 | Tran ..................... A61B 5/0013 340/539.11 |
| 2016/0210838 | A1 | 7/2016 | Yan et al. |
| 2016/0270717 | A1* | 9/2016 | Luna .................... A61B 5/743 |
| 2016/0270740 | A1* | 9/2016 | Raisoni ................ A61B 5/1459 |
| 2016/0345874 | A1* | 12/2016 | Raisoni ................ A61M 5/1723 |
| 2017/0041699 | A1* | 2/2017 | Mackellar ........... H04R 1/1075 |
| 2017/0076630 | A1 | 3/2017 | Angelides et al. |
| 2017/0228514 | A1* | 8/2017 | Apte ...................... G06F 19/00 |
| 2017/0270508 | A1 | 9/2017 | Roach et al. |
| 2018/0013571 | A1 | 1/2018 | Aarnio et al. |
| 2018/0182472 | A1 | 6/2018 | Preston et al. |
| 2018/0220890 | A1* | 8/2018 | Bardy .................... A61B 5/363 |
| 2018/0226150 | A1* | 8/2018 | Hayter ................. G16H 40/63 |
| 2018/0286510 | A1 | 10/2018 | Liang et al. |
| 2019/0038236 | A1* | 2/2019 | Hays .................... A61B 5/0022 |
| 2019/0043501 | A1* | 2/2019 | Ramaci ................. G16H 40/67 |
| 2019/0074090 | A1* | 3/2019 | Ronen .................. G06Q 10/067 |
| 2020/0359913 | A1* | 11/2020 | Ghodrati ............... A61B 5/747 |
| 2021/0217522 | A1* | 7/2021 | Loscutoff .............. G16H 40/67 |

FOREIGN PATENT DOCUMENTS

| WO | WO 2012/174303 A1 | 12/2012 |
| WO | WO 2014/210201 A1 | 12/2014 |
| WO | WO 2016/183389 A1 | 11/2016 |
| WO | WO 2018/220445 A1 | 12/2018 |
| WO | WO 2019/010266 A1 | 1/2019 |
| WO | WO 2019/048875 A1 | 3/2019 |

OTHER PUBLICATIONS

U.S. Appl. No. 16/800,034, filed Feb. 25, 2020, Chen, et al.
U.S. Appl. No. 16/800,052, filed Feb. 25, 2020, Kendale.
U.S. Appl. No. 16/800,080, filed Feb. 25, 2020, Kozin, et al.
U.S. Appl. No. 16/800,092, filed Feb. 25, 2020, Kozin, et al.
U.S. Appl. No. 16/800,115, filed Feb. 25, 2020, Bridgewater, et al.
U.S. Appl. No. 16/800,144, filed Feb. 25, 2020, Boulos, et al.

* cited by examiner

| Time | Parameter 1 | Parameter 2 | ... | Parameter n |
|------|-------------|-------------|-----|-------------|
| t    |             |             |     |             |
| t-1  |             |             |     |             |
| ...  |             |             |     |             |
| t-n  |             |             |     |             |

FIG. 3B

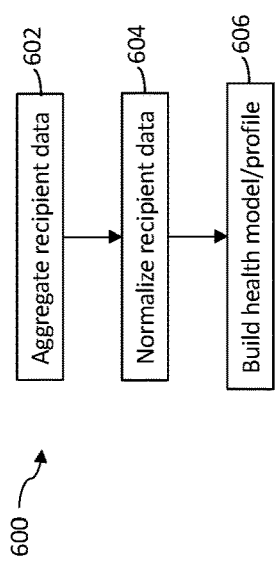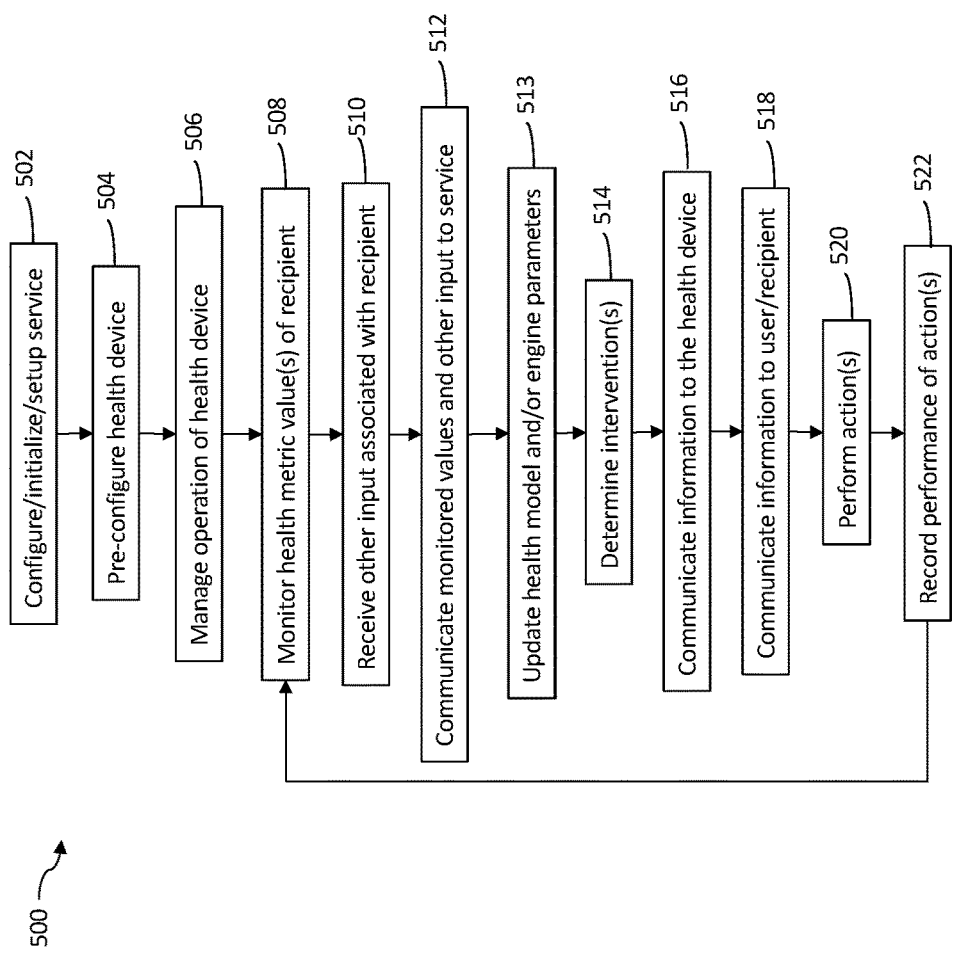

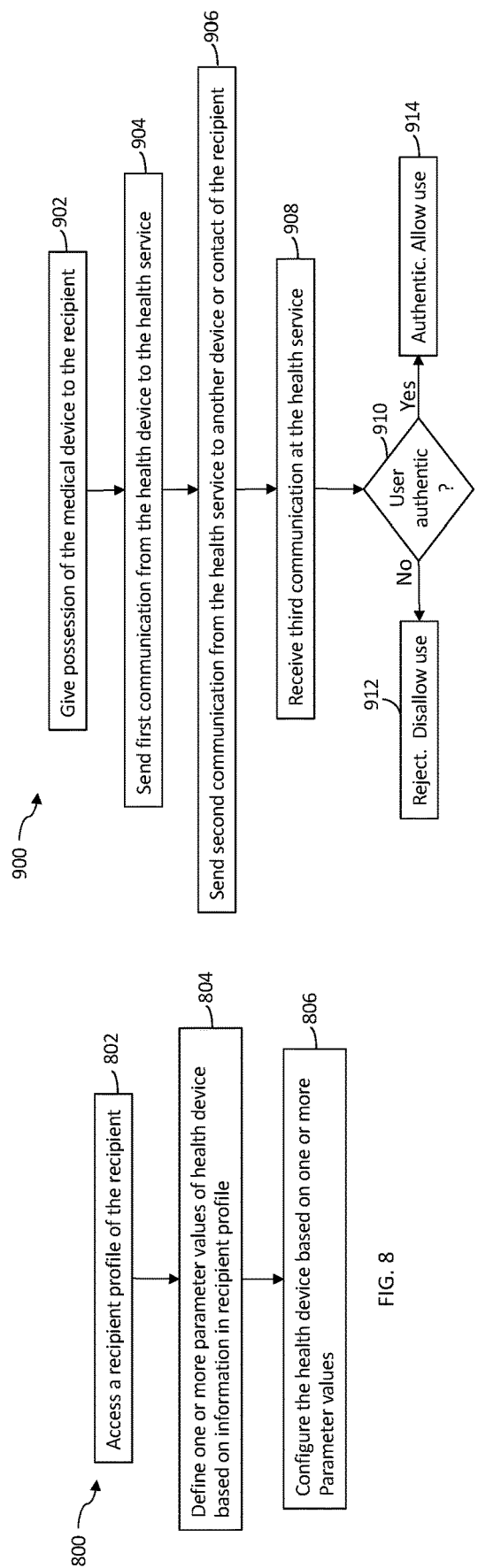

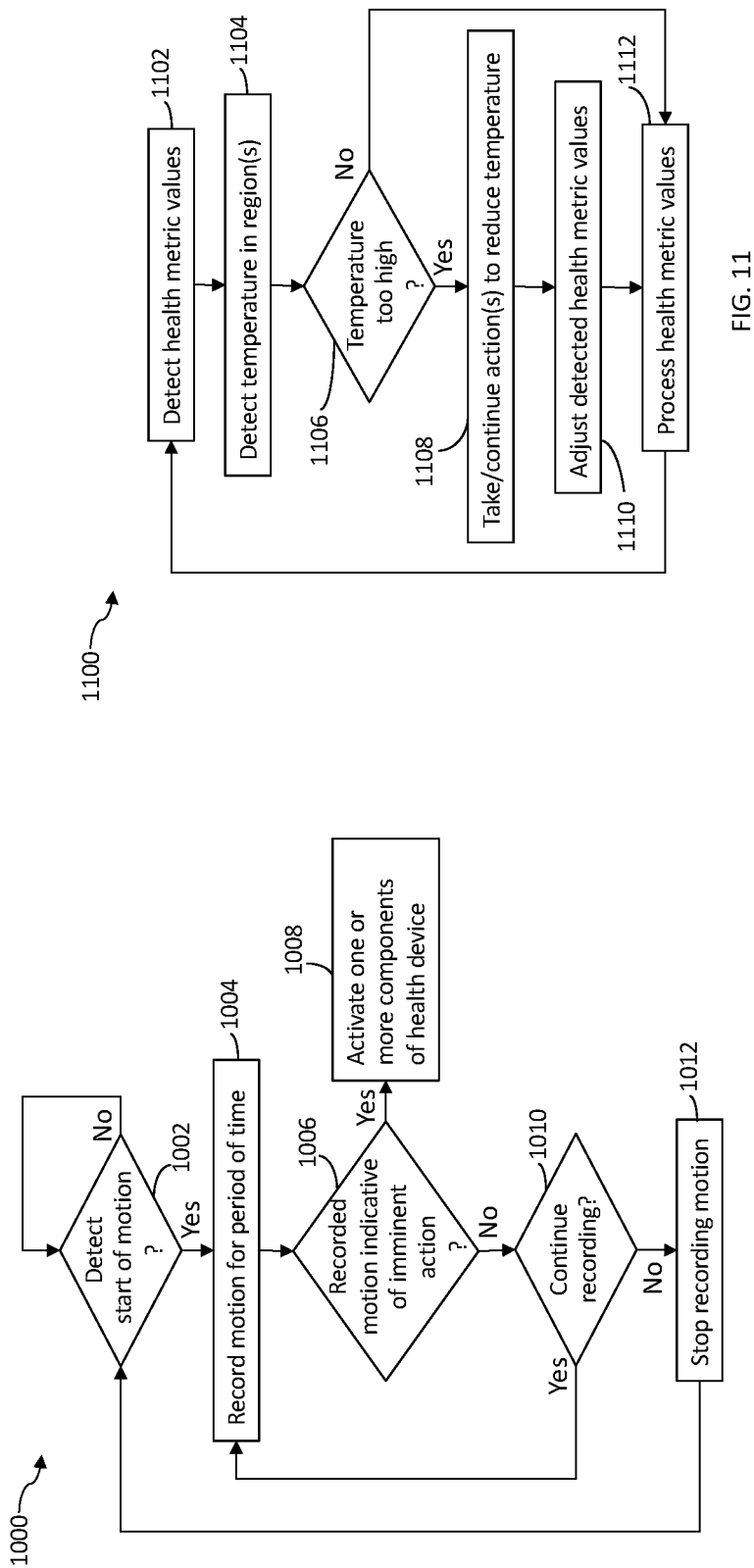

MANAGING AUDIO FOR REMOTE HEALTH SERVICES

CROSS-REFERENCE TO RELATED APPLICATIONS

This application claims priority to U.S. provisional patent application No. 62/858,759 filed on Jun. 7, 2019, titled "A NETWORK CONNECTED MEDICAL MONITORING DEVICE WITH TEXT, AUDIO AND VIDEO COMMUNICATIONS," and U.S. provisional patent application No. 62/865,411 filed on Jun. 24, 2019, titled "A SYSTEM FOR SELECTING AND DELIVERING HEALTH INTERVENTIONS," both of which are incorporated by reference herein.

TECHNICAL FIELD

This application is directed to the field of health services, and more particularly to remotely providing health services to a recipient using a mobile device, including autonomously selecting and communicating health information to a recipient as part of providing health services to the recipient, including, for example, specifying actions to perform.

BACKGROUND OF THE INVENTION

The Centers for Disease Control and Prevention estimate that six out of ten adults in the US have a chronic disease, while four out of ten have two or more chronic diseases. Two of the most widespread chronic conditions are hypertension and diabetes. According to recent reports by the American Heart Association based on updated hypertension guidelines, almost half of US adults (46%) suffer from hypertension, and the overall number of people with high blood pressure exceeds 100 million. According to such reports, the number of deaths caused by hypertension increased by 38% through the period 2005-2015. On average, national medical costs associated with hypertension have been estimated at about $131 billion in annual healthcare expenditure. According to some reports, over 30 million Americans, or 9.4% of the population, have diabetes (approximately 1.25 million American children and adults have type 1 diabetes); it is estimated that 7.2 million of those are undiagnosed. According to some reports, the percentage of Americans age 65 and older with diabetes remains high, at 25.2%, or 12.0 million seniors (diagnosed and undiagnosed), and diabetes remains the 7th leading cause of death in the United States; in 2015, 79,535 death certificates listed it as the underlying cause of death, and a total of 252,806 death certificates listing diabetes as an underlying or contributing cause of death. According to some reports, total healthcare costs of diagnosed diabetes are at $327 billion, of which $237 billion are attributed to direct medical costs and $90 billion to reduced productivity. Diabetes is closely related to hypertension: according to multiple studies, over 70% of diabetes patients have high blood pressure.

Chronic medical conditions like hypertension and diabetes require frequent (e.g., continuous) monitoring. There are multiple technologies and medical monitoring devices on the market and in development for measuring blood pressure and blood glucose levels. These products are characterized by a broad range of features, accuracy, usability, integration with other devices, connectivity, levels of support offered to patients, price, insurance coverage, etc. Conventional blood pressure monitors may use an upper arm cuff, but wrist monitors are also present on the market. Top digital blood pressure monitors on the market may offer extensive memory, automatic averaging by multiple measurements, different types of displays and Bluetooth connectivity with a smartphone, which may receive, store and process blood pressure data and may offer applications for advanced blood pressure analytics.

Glucometers measure blood glucose levels. There are two basic well-known types of glucometers for diabetes patients: glucometers with separate test strips for periodic testing of glucose levels by a patient and continuous glucose monitoring (CGM) devices, which typically have an implanted subcutaneous sensor, wireless transmitter and receiver, and automatic measurement system, and which optionally may be combined with an insulin pump.

Most patients are capable of measuring their own blood pressure or glucose level with devices at home. In some cases, a patient may take a particular action based on the measurements. For instance, a patient may administer themselves an insulin injection if their blood glucose level is in a particular range. In extreme instances, a patient may contact medical professionals if the home measurements are outside specific limits. There are instances where the home measurements may indicate a benefit of a moderate correction/adjustment (e.g., a blood glucose measurement indicating that a patient should eat a piece of fruit), but most patients, unless they have had significant training, are probably unable to accurately determine if an adjustment/correction would be useful or what the adjustment/correction would be. Although a patent obtaining periodic measurements at home could contact a medical professional for guidance after each measurement, this is usually not practical for a number of reasons, including cost.

Accordingly, it is desirable to provide a practical mechanism for providing guidance to patients that measure their own blood pressure or glucose level with devices at home.

SUMMARY OF THE INVENTION

According to the system described herein, remotely providing a first health service to a person for a health condition includes predefining a plurality of analysis types, each analysis type representing a type of analysis to be performed on information about the person to determine an intervention as part of providing a health service, predefining a first rule specifying a condition under which to apply a first of the plurality of analysis types, performing the first health service on the person, including detecting health values of one or more health metrics of the person associated with performance of the first health service, selecting the first analysis type to perform based on the first rule and information about the person, including the health values, performing a first type of analysis on the information to determine what interventions to be undertaken based on the information as part of performing the first health service, and remotely communicating a determined intervention to the person. A part of the first health service may be performed by a first health device locally coupled to the person, remotely providing a first health service to a person for a health condition may further include the first health device detecting the health values and transmitting the health values to a second device remotely located from the first health device, where the second device remotely communicates the determined intervention to the first health device, and the first health device performs a first action based on the remote communication. The intervention may include altering a health treatment administered to the person as part of the first health service. Remotely providing a first health service to a person for a health condition may also include predefining a plurality of communication types, including a notification, an instruction, an inquiry, feedback, a live conversation and an automated conversation, where performing the first type of analysis on the information includes determining a first communication type from among the plurality of communication types for the communication, and where the intervention is remotely communicated as a communication of the first communication type. Remotely providing a first health service to a person for a health condition may also include predefining a plurality of media types, including text, audio, images and video, where performing the first type of analysis on the information includes determining one or more of the plurality of media types with which to communicate with the person, and where the intervention is remotely communicated to the person using the media types. The first analysis type may be autonomous analysis based on machine learning and/or based on predefined rules.

According further to the system described herein, a system remotely provides a first health service to a person for a health condition based on remotely detected values of health metrics of the person associated with performance of the first health service. The system includes one or more processors and a memory having code stored thereon that, when executed, predefines a plurality of analysis types, each analysis type representing a type of analysis to be performed on information about the person to determine an intervention as part of providing a health service, predefines a first rule specifying a condition under which to apply a first of the plurality of analysis types, selects the first analysis type to perform based on the first rule and on information about the person, including the one or more detected values, performs a first type of analysis on the information to determine what interventions to be undertaken based on the information as part of performing the first health service, and remotely communicates a determined intervention to the person. A part of the first health service may be performed by a first health device locally coupled to the person and the first health device may detect the detected values and transmit the one or more detected values to a second device remotely located from the first health device, the second device remotely communicating the determined intervention to the first health device, and the first health device performing a first action based on the remote communication. The determined intervention may include altering a health treatment administered to the person as part of the first health service. A plurality of communication types may be predefined to include a notification, an instruction, an inquiry, feedback, a live conversation and an automated conversation and performing the first type of analysis on the information may include determining a first communication type from among the plurality of communication types for the communication, the determined intervention being remotely communicated as a communication of the first communication type. A plurality of media types may be predefined to include text, audio, images and video and performing the first type of analysis on the information may include determining one or more of the plurality of media types with which to communicate with the person, the determined intervention being remotely communicated to the person using the media types. The first analysis type may be autonomous analysis based on machine learning and/or on predefined rules.

According further to the system described herein, non-transitory computer-readable media has software stored thereon that remotely provides a health service to a person for a health condition based on remotely detected values of health metrics of the person associated with performance of the health service. The software includes executable code that defines a plurality of analysis types, each analysis type representing a type of analysis to be performed on information about the person to determine an intervention as part of providing the health service, executable code that defines a first rule specifying a condition under which to apply a first of the plurality of analysis types, executable code that selects the first analysis type to perform based on the first rule and on information about the person, including the one or more detected values, executable code that performs a first type of analysis on the information to determine what interventions to be undertaken based on the information as part of performing the first health service, and executable code that remotely communicates a determined intervention to the person. At least part of the first health service may be performed by a first health device locally coupled to the person and the software may further include executable code that controls the first health device to detect the values and transmits the values to a second device remotely located from the first health device, where the second device remotely communicates the determined intervention to the first health device, and the first health device performs an action based on the remote communication. The first intervention may include altering a health treatment administered to the person as part of the first health service. The software may further include executable code that predefines a plurality of communication types, including a notification, an instruction, an inquiry, feedback, a live conversation and an automated conversation, where performing the first type of analysis on the information includes determining a first communication type from among the plurality of communication types for the communication, and where the determined intervention is remotely communicated as a communication of the first communication type. The software may further include executable code that predefines a plurality of media types, including text, audio, images and video, where performing the first type of analysis on the information includes determining one or more of the plurality of media types with which to communicate with the person, and where the at least first intervention is remotely communicated to the person using the one or more media types. The first analysis type may be autonomous analysis based at least in part on machine learning.

According further to the system described herein, a mobile health device includes a sensor that monitors values of a health metric of a person, a control component that controls the mobile health device to perform actions as part of providing a health service, where the control component includes an input that receives audio signals corresponding to the monitored values of the health metric, and produces a control signal based on information about the person, including the monitored values of the health metric of the person, and components of the mobile health device that receive the control signal and perform an action to provide the health service based on the control signal, where the components include user output components for producing sound and/or displaying information and where providing the health service includes playing information as sound, displaying information as text, displaying information as motion video, and/or displaying information still images. The mobile health device may also include a network interface component that communicates with a remote device that is remotely coupled to the mobile health device as part of providing the health service. The network interface component may communicate the monitored values to the remote device, which has an audio capture device that captures voice signals corresponding to the monitored values of the health metric. The network interface component may receive communications from the remote device that include encoded audio information corresponding to the provided health service and the mobile health device may further include an audio player that produces decoded audio signals from the encoded audio information and a speaker that produces sound from the decoded audio signals. The encoded audio information may include encoded voice signals of a health practitioner. The mobile health device may also include an audio capture device that captures voice signals of the person, an audio encoding component that encodes the captured voice signals, and telephony logic communicatively coupled to the network interface component, the audio encoding component and the audio player that controls the exchange of real-time voice communications between the health professional and the person. The mobile health device may also include an audio capture device that captures voice signals corresponding to the monitored values of the health metric from which the audio input signals are produced. The mobile health device may also include a speech-to-text conversion module that converts voice signals to text associated with the health service, where the network interface component transmits information corresponding to the monitored values of the health metric based on the text. The health metric may be a blood pressure level and/or blood glucose level. The control component may convert each received audio signal to an input value and determine the control signal based on the input value.

According further to the system described herein, for a mobile health device including a sensor that monitors values of a health metric of a person, a control component that controls the mobile health device to perform actions as part of providing a first health service, where the control component includes an input that receives audio signals corresponding to the monitored values of the health metric, and produces a control signal to control components of the mobile health device, and components that receive the control signal and perform an action based on the control signal as part of providing the health service, where the components include user output components that produce sound and/or display information, operating the mobile health device includes determining which of the following output actions to perform in providing the health service based on information about the person, including the monitored values of the health metric of the person, playing information as sound on the user output components, displaying information as text on the user output components, displaying information as motion video on the user output components, and displaying information as still images on the user output components, and the control component controlling the user output components to perform a determined user output action. A network interface component may exchange communications with a remote device that is remotely coupled to the mobile health device as part of providing the health service, where the network interface component receives communications from the remote device. The network interface component may communicate the monitored values to the remote device, the remote device including an audio capture device that captures voice signals corresponding to the monitored values of the health metric from which the audio input signals are produced. The network interface component may receive communications from the remote device that include encoded audio information corresponding to the provided health service, where the mobile health device may further include an audio player that produces decoded audio signals from the encoded audio information and may include a speaker that produces sound from the decoded audio signals. The encoded audio information may include encoded voice signals of a health practitioner. Determining output actions to perform may further include capturing voice signals of the person, encoding the captured voice signals, and exchanging real-time voice communications between the health practitioner and the person. Determining output actions to perform may further include capturing voice signals corresponding to monitored values of the health metric from which the first audio input signals are produced. Determining output actions to perform may further include converting voice signals to text associated with the provided first health service corresponding to the detected health metric and transmitting information corresponding to the monitored values of the health metric based on the text. The health metric may be a blood pressure level and/or blood glucose level.

According further to the system described herein, for a mobile health device including a sensor that monitors values of a health metric of a person, a control component that controls the mobile health device to perform one or more actions as part of providing a health service, where the control component includes an input that receives first audio signals corresponding to monitored values of the health metric, and produces a control signal to control components of the mobile health device, and components that receive the control signal and perform an action based on the control signal as part of providing the health service, where the components include user output components for producing sound and/or displaying information, non-transitory computer-readable media having software stored thereon includes executable code that determines which one or more of the following output actions to perform to provide the health service based on information about the person, including the monitored values of the health metric of the person, playing information as sound on the user output components, displaying information as text on the user output components, displaying information as motion video on the user output components, and displaying information as still images on the user output components, and executable code within the control component that controls the user output components to perform the determined user output actions.

According further to the system described herein, deploying a mobile health device to provide a health service for a person for a health condition includes accessing a profile of the person, defining a value for a first parameter of the mobile health device based on the profile, configuring the mobile health device based on the value of the first parameter, and giving possession of the mobile health device to the person. Deploying a mobile health device to provide a health service for a person for a health condition may also include, after giving possession of the mobile health device, receiving a first communication from the mobile health device, in response to receiving the first communication, sending a second communication to a second device associated with the person, receiving a third communication, and authenticating that an operator in possession of the mobile health device is the person based on receipt of the third communication. The second communication may include an access code, where the third communication is from the mobile health device and includes the access code, and where authenticating is based on the third communication including the access code. The third communication may be from the second device, and authenticating may be based on the third communication being received from the second device. Deploying a mobile health device to provide a health service for a person for a health condition may also include creating the profile for the person at a time of purchase or order of the mobile health device. The profile may include a first parameter value specific to the person and associated with a health condition of the person. The mobile health device may include a health sensor for monitoring a value of a health metric of the person the first parameter value may be specific to the health sensor.

According further to the system described herein, a system for deploying a mobile health device to provide a health service for a person having a health condition includes one or more processors and a memory having code stored thereon that, when executed, accesses a profile of the person, defines a value for a first parameter of the mobile health device based on the profile, and configures the mobile health device based on the value of the first parameter. The code, when executed, may receive a first communication from the mobile health device after the person takes possession of the mobile health device, send a second communication to a second device associated with the person in response to receiving the first communication, receive a third communication, and, based on receipt of the third communication, authenticate that an operator in possession of the mobile health device is the person. The second communication may include an access code, the third communication may be from the mobile health device and may include the access code, and the authenticating may be based on the third communication including the access code. The third communication may be from the second device, and authenticating may be based on the third communication being received from the second device. The code, when executed, may create the profile for the person at a time of purchase or order of the mobile health device. The profile may include a first parameter value specific to the person and associated with the health condition of the person. The mobile health device may include a health sensor for monitoring a value of a health metric of the person, and the first parameter value may be specific to the health sensor.

According further to the system described herein, non-transitory computer-readable media has software stored thereon that deploys a mobile health device to provide a health service for a person with a health condition. The software includes executable code that accesses a profile of the person, executable code that defines a value for a first parameter of the mobile health device based on the profile, and executable code that, prior to possession of the mobile health device being given to the person, configures the mobile health device based on the value of the first parameter. The software may also include executable code that, after possession of the mobile health device has been given to the person, receives a first communication from the mobile health device, executable code that, in response to receiving the first communication, sends a second communication to a second device associated with the person, executable code that receives a third communication, and executable code that authenticates that an operator in possession of the mobile health device is the person based on receipt of the third communication. The second communication may include an access code, the third communication may be from the mobile health device and include the access code, and authenticating may be based on the third communication including the access code. The third communication may be from the second device, and the authenticating may be based on the third communication being received from the second device. The software may also include executable code that creates the profile for the person at a time of purchase or order of the mobile health device. The mobile health device may include a health sensor for monitoring a value of a health metric of the person, and the profile may include a first parameter value specific to the health sensor.

According further to the system described herein, for a system including a mobile health device locally coupled to a person and a remote device remotely coupled to the mobile health device, remotely providing a health service to a person for a health condition includes the remote device determining a health condition for which the health service is being provided, the remote device sending a first communication to the mobile health device requesting that the mobile health device capture visual information associated with the health condition, the mobile health device capturing the visual information associated with the health condition, and the mobile health device transmitting the visual information to the remote device. The mobile health device may include a health sensor for monitoring values of a health metric and remotely providing a health service to a person for a health condition may also include the mobile health device detecting values of the health metric and transmitting a second communication from the mobile health device to the remote device, where determining the health condition and sending the first communication may be performed by the remote device in response to receiving the second communication. Prior to capturing the visual information, remotely providing a health service to a person for a health condition may also include detecting one or more images, applying image recognition techniques to determine whether the one or more images satisfy the visual information requested, and, if the one or more images satisfy the visual information requested, instructing a user of the health device to capture the visual information. Remotely providing a health service to a person for a health condition may also include, after capturing the visual information, applying image recognition techniques to images of the captured visual information to determine whether the images satisfy the visual information requested, and, if the images do not satisfy the visual information requested, indicating to a user that the images do not satisfy the visual information requested. The visual information may be video and/or a still image. The first communication may include instructions for capturing the visual information. The instructions may be provided to the person to use the mobile health device to capture the visual information.

According further to the system described herein, a system for remotely providing a health service to a person for a health condition includes a mobile health device locally coupled to the person and a remote device remotely coupled to the mobile device and having one or more processors and a memory with code stored thereon that, when executed, determines the health condition for which the health service are being provided, and sends a first communication to the mobile health device requesting that the mobile health device capture visual information associated with the health condition, where the mobile health device includes one or more processors and a memory having code stored thereon that controls the mobile health device to capture the visual information associated with the health condition and transmit the visual information to the remote device. The mobile health device may detect values of a health metric and transmit a second communication to the remote device, and determining the health condition and sending the first communication may be performed by the remote device in response to receiving the second communication. Prior to capturing the visual information, the mobile health device may detect images, apply image recognition techniques to determine whether the images satisfy the visual information requested and, if the images satisfy the visual information requested, instruct a user of the health device to capture the visual information. After capturing the visual information, image recognition techniques may be applied to images of the captured visual information to determine whether the images satisfy the visual information requested, and, if the images do not satisfy the visual information requested, the mobile health device may indicate to a user that the images do not satisfy the visual information requested. The visual information may be a still image. The first communication may include instructions for the person to capture the visual information. The person may control the mobile health device to capture the visual information in accordance with the instructions.

According further to the system described herein, for a system including a mobile health device locally coupled to a person and to a remote device remotely coupled to the mobile health device, non-transitory computer-readable media has software stored thereon for providing a health service to the person for a health condition. The software includes executable code that controls the remote device to determine the health condition for which the health service is being provided, and send a first communication to the mobile health device requesting that the mobile health device capture visual information associated with the health condition and executable code that controls the mobile health device to capture the visual information associated with the health condition and transmit the visual information to the remote device. The mobile health device may include a health sensor for monitoring values of a health metric and the software may further include executable code that controls the mobile health device to detect values of the health metric and transmit a second communication from the mobile health device to the remote device, where determining the health condition and sending the first communication may be performed by the remote device in response to receiving the second communication. Images may be detected prior to capturing the visual information and the software may further include executable code that applies image recognition techniques to determine whether the images satisfy the visual information requested and executable code that, if the images satisfy the visual information requested, indicates to a user of the health device to capture the visual information. The software may further include executable code that, after the visual information is captured, applies image recognition techniques to images of the captured visual information to determine whether the images satisfy the visual information requested and executable code that, if the images do not satisfy the visual information requested, indicates to a user that the images do not satisfy the visual information requested. The first communication may include instructions for the person for capturing the visual information, and the person may control the mobile health device to capture the visual information in accordance with the instructions.

According further to the system described herein, a mobile health device for providing a health service for a person includes a health sensor that monitors values of a health metric of the person, a power control component that controls supplying power to the health sensor and to other components of the mobile health device, and a motion sensor, coupled to the power control component, that detects a motion of the mobile health device, where the motion sensor sends a communication to the power control component in response to detection of the motion to activate the other components of the mobile health device. The communication may specify a duration of the motion, and the power control component may activate at least one of the other components of the mobile health device based on the duration. The communication may specify a direction of the motion, and the power control component may activate at least one of the other components of the mobile health device based on the direction. The other components may include a network interface component that communicates with a remotely coupled device to provide the health service to the person. The communication may be generated based on a comparison between the motion and a motion profile indicative of motion patterns associated with the health device. The mobile health device may be a hand-held device. The health sensor may have a physical interconnect for connecting with a health accessory employed by the health sensor to monitor values of health metrics, and the communication may be generated based on detection of the health accessory becoming connected to the physical interconnect.

According further to the system described herein, for a mobile health device including a health sensor that monitors values of health metrics of a person, and a power control component that controls supplying power to the health sensor and to other components of the mobile health device, providing a health service for the person includes detecting motion of the mobile health device, sending a communication to the power control component corresponding to detection of the motion, and the power control component activating at least one of the other components of the mobile health device based on a communication. The communication may specify a duration of the motion, and the power control component may activate the at least one of the other components based on the duration. The communication may specify a direction of the motion, and the power control component may activate the at least one of the other components based on the direction. The at least one of the other components may include a network interface component that communicates with a remotely coupled device to provide the health service to the person. The health device may have a motion profile indicative of motion patterns associated with the health device and providing a health service for the person may include comparing the motion to the motion profile and generating the communication based on the comparison. The mobile health device may be a hand-held device. The health sensor may have a physical interconnect for connecting with a health accessory employed by the health sensor to monitor the values of the health metric and providing a health service for the person may include detecting when the health accessory becomes connected to the physical interconnect, where the communication may be generated based on detection of the health accessory becoming connected to the physical interconnect.

According further to the system described herein, for a mobile health device including a health sensor that monitors values of health metrics of a person, and a power control component that controls supplying power to the health sensor and to other components of the mobile health device, non-transitory computer-readable media has software stored thereon that provides a health service for a person. The software includes executable code that detects a motion of the mobile health device, executable code that sends a communication to the power control component corresponding to detection of the motion, and executable code that controls the power control component to activate at least one of the other components of the mobile health device based on the communication. The communication may specify a duration of the motion, and the power control component may activate the at least one of the other components of the mobile health device based on the duration. The communication may specify a direction of the motion, and the power control component may activate the at least one of the components of the mobile health device based on the direction. At least one of the components may include a network interface component that communicates with a remotely coupled device to provide the health service to the person. The health device may have a motion profile indicative of motion patterns associated with the health device and the software may further include executable code that compares the motion to the motion profile and executable code that generates the communication based on the comparison. The health sensor may have a physical interconnect for connecting with a health accessory employed by the health sensor to monitor the values of the health metric and the software may further include executable code that detects when the health accessory becomes connected to the physical interconnect, and executable code that generates the communication based on detection of the health accessory becoming connected to the physical interconnect.

According further to the system described herein, a mobile health device for providing a health service for a person includes a health sensor that monitors values of health metrics of the person, where performance of the health sensor is affected by temperature, an internal temperature sensor that monitor a temperature of an internal region of the mobile health device, and a thermal control component that controls a thermal output of one or more components of the mobile health device based at least in part on the temperature of the one or more internal regions of the health sensor. The mobile health device may also include a plurality of processing cores that execute instructions where the thermal control component reduces a collective thermal output of the plurality of processing cores by reducing a number of the plurality of the processing cores that actively execute instructions. The mobile health device may also include a processing core that executes instructions, where the thermal control component reduces a thermal output of the processing core by reducing a frequency of instruction execution of the processing core. The mobile health device may also include an external temperature sensor that monitors a temperature of an external region that is external to the mobile health device and compensation logic that determines a difference between a monitored internal temperature value and a monitored external temperature value, and modifies monitored health metric values based on a determined difference. The mobile health device may also include a thermal buffer between the health sensor and an other component of the mobile health device that generate heat during operation of the mobile health device, the thermal buffer being arranged to thermally insulate the health sensor from the other component.

According further to the system described herein, for a mobile health device including a health sensor, a temperature sensor and a thermal control component, providing a health service for a person includes the health sensor monitoring values of health metrics of the person, where performance of the health sensor is affected by temperature, the internal temperature sensor monitoring a temperature of an internal region of the mobile health device, and a thermal control component controlling a thermal output of components of the mobile health device based on the monitored temperature of the internal region of the health sensor. The mobile health device may further include a plurality of processing cores that execute instructions and providing a health service for a person may also include the thermal control component reducing a collective thermal output of the plurality of processing cores by reducing a number of the plurality of the processing cores that actively execute instructions. The mobile health device may further include a processing core that executes instructions and providing a health service for a person may also include the thermal control component reducing a thermal output of the processing core by reducing a frequency of instruction execution of the processing core. The mobile health device further includes an external temperature sensor and providing a health service for a person may also include the external temperature sensor monitoring a temperature of an external region that is external to the mobile health device, determining a difference between a monitored internal temperature value and a monitored external temperature value, and modifying one or more monitored health metric values based at least in part on the determined difference. The mobile health device may include a thermal buffer between the health sensor and an other component that generates heat during operation of the mobile health device and the thermal buffer may be arranged to thermally insulate the health sensor from the other component.

According further to the system described herein, for a mobile health device including a health sensor, a temperature sensor and a thermal control component, non-transitory computer-readable media has software stored thereon that provides a health service for a person. The software includes executable code that controls the health sensor to monitor values of health metrics of the person, where performance of the health sensor is affected by temperature, executable code that controls the internal temperature sensors to obtain a temperature for an internal region of the mobile health device, and executable code that controls a thermal control component to control a thermal output of components of the mobile health device based on the monitored temperature of the internal region of the health sensor. The mobile health device may further include a plurality of processing cores that execute instructions and the software may further include executable code that controls the thermal control component to reduce a collective thermal output of the plurality of processing cores by reducing a number of the plurality of the processing cores that actively execute instructions. The mobile health device may further include a processing core that executes instructions and the software may further include executable code that controls the thermal control component to reduce a thermal output of the processing core by reducing a frequency of instruction execution of the processing core. The mobile health device may further include an external temperature sensor and the software may further executable code that, for an external region that is external to the mobile health device, controls the external temperature sensor to monitor a temperature of the external region, executable code that determines a difference between a monitored internal temperature value and a monitored external temperature value, and executable code that modifies monitored health metric values based on the determined difference. The mobile health device may include a thermal buffer between the health sensor and an other component that generates heat during operation of the mobile health device and the thermal buffer may be arranged to thermally insulate the health sensor from the other component.

According further to the system described herein, providing to a person a health service for a health condition includes receiving, from a health sensor of a mobile health device over an initial period, a plurality of initial values of health metrics of the person associated with performance of the health service, determining, based on the initial values, baseline values of the health metrics for the person, receiving, from the health sensor at a time after the initial period, an additional value corresponding to at least one of the health metrics, and determining whether the additional value represents an irregularity with respect to the baseline values for the person. Providing to a person a health service for a health condition may also include, if it is determined that the additional value represents an irregularity with respect to the baseline values, communicating the irregularity to a provider of the health service. Providing to a person a health service for a health condition may also include, if it is determined that the additional value represent an irregularity with respect to the baseline values, communicating the irregularity to an operator of the mobile health device. Providing to a person a health service for a health condition may also include receiving input from the operator through a user interface of the mobile health device to address the irregularity. Providing to a person a health service for a health condition may also include the mobile health device communicating the initial values and the additional value to a remote device remotely coupled to the mobile health device and the remote device determining the baseline values and determining whether the additional value represents an irregularity with respect to the baseline values. Providing to a person a health service for a health condition may also include, if the remote device determines that the additional value represent an irregularity with respect to the baseline values, the remote device communicating the irregularity to an operator of the mobile health device, where the mobile health device receiving the additional value, determining whether the additional value represents an irregularity, and communicating the irregularity are performed in real-time. Determining baseline values of the health and determining whether the additional value represents an irregularity may be performed by the mobile health device.

According further to the system described herein, a system for providing a health service to a person for a health condition includes one or more processors and a memory having code stored thereon that, when executed, receives, from a health sensor of a mobile health device over an initial period, a plurality of initial values of health metrics of the person associated with performance of the health service, determines, based on the initial values, baseline values of the health metrics for the person, receives, from the health sensor at a time after the initial period, an additional value corresponding to at least one of the health metrics, and determines whether the additional value represent an irregularity with respect to the baseline values for the person. If it is determined that the additional value represents an irregularity with respect to the baseline values, the irregularity may be communicated to a provider of the health service. If it is determined that the additional value represents an irregularity with respect to the baseline values, the irregularity may be communicated to an operator of the mobile health device. Input from the operator may be received through a user interface of the mobile health device to address the irregularity. The mobile health device may communicate the initial values and the additional value to a remote device remotely coupled to the mobile health device and the remote device may determine the baseline values and determine whether additional value represent an irregularity with respect to the baseline values. If the remote device determines that the additional value represent an irregularity with respect to the baseline values, the remote device may communicate the irregularity to an operator of the mobile health device. Receiving the additional value, determining whether the additional value represent an irregularity, and communicating the irregularity may all be performed in real-time.

According further to the system described herein, non-transitory computer-readable media has software stored thereon for providing a person with a health service for a health condition. The software includes executable code that receives, from a health sensor of a mobile health device over an initial period, a plurality of initial values of health metrics of the person associated with performance of the health service, executable code that determines, based on the initial values, baseline values of the health metrics for the person, executable code that receives, from the health sensor at a time after the initial period, an additional value corresponding to at least one of the health metrics, and executable code that determines whether the additional value represents an irregularity with respect to baseline values for the person. The software may further include executable code that, if it is determined that the additional value represents an irregularity with respect to the baseline values, communicates the irregularity to a provider of the health service. The software may further include executable code that, if it is determined that the additional value represents an irregularity with respect to the baseline values, communicates the irregularity to an operator of the mobile health device. The software may further include executable code that receives input from the operator through a user interface of the mobile health device to address the irregularity. The software may further include executable code that controls the mobile health device to communicate the initial values and the additional value to a remote device coupled to the mobile health device and executable code that controls the remote device to determine the initial values and to determine whether the additional value represent an irregularity with respect to the baseline values. The software may further include executable code that, if the remote device determines that the additional value represents an irregularity with respect to the baseline values, controls the remote device to communicate the irregularity to an operator of the mobile health device, where receiving the values, determining whether the additional values represent an irregularity, and communicating the irregularity are performed in real-time.

According further to the system described herein, remotely providing a health service to a person for a health condition includes receiving at a device, in real time, values of a health metric detected by a health device locally coupled to the person and remotely coupled to the device, applying automated machine learning in real-time to the values and to historical information specific to the person, including information corresponding to the health condition, to determine an intervention as part of providing the health service, the intervention including performance of a determined action, and sending a communication from the device to the health device directing performance of the determined action. Remotely providing a health service to a person for a health condition may also include determining a time at which to perform the determined action, where the communication indicates the time at which to perform the determined action. Remotely providing a health service to a person for a health condition may also include determining whether an expiration time for the determined action has been reached and preventing or halting the determined action based on determining that the expiration time has been reached. Remotely providing a health service to a person for a health condition may also include generating a preliminary list of actions based on the values and on the historical information, comparing the preliminary list to a list of safe actions, and removing from the preliminary list any action that is not on the list of safe actions to produce a safe list of actions that includes the determined action. Remotely providing a health service to a person for a health condition may also include generating a preliminary list of actions based on the values and on the historical information, determining a best action from the preliminary list, and sending a communication from the device to the health device directing performance of the best action.

According further to the system described herein, a system for remotely providing a health service to a person for a health condition includes one or more processors and a memory having code stored thereon that, when executed, receives at a device, in real time, values of a health metric detected by a health device locally coupled to the person and remotely coupled to the device, applies automated machine learning in real-time to the values and to historical information specific to the person, including information corresponding to the health condition, to determine an intervention as part of providing the first health service, the intervention including performance of a determined action, and sends a communication from the device to the health device directing performance of the determined action. The communication may indicate a time at which to perform the determined action. The code may determine whether an expiration time for the determined action has been reached and may prevent or halt the determined action based on the determination that the expiration time has been reached. The code may generate a preliminary list of actions based on the values and the historical information, compare the preliminary list to a list of safe actions, and remove from the preliminary list any action that is not on the list of safe actions to produce a safe list of actions that includes the determined action. The code may generate a preliminary list of actions based on the values and the historical information, determine at least one best action from the preliminary list, and send a communication from the device to the health device directing performance of the best action.

According further to the system described herein, non-transitory computer-readable media has software stored thereon for remotely providing a health service to a person for a health condition. The software includes executable code that receives at a device, in real time, values of a health metric detected by a health device locally coupled to the person and remotely coupled to the device, executable code that applies automated machine learning in real-time to the values and to historical information specific to the person, including information corresponding to the health condition, to determine an intervention as part of providing the first health service, the intervention including performance of a determined action, and executable code that sends a communication from the device to the health device directing performance of the determined action. The software may further include executable code that determines a time at which to perform the determined action, where the communication indicates the time at which to perform the determined action. The software may further include executable code that determines whether an expiration time for the determined action has been reached and executable code that prevents or halts the determined action based on the determination that the expiration time has been reached. The software may further include executable code that generates a preliminary list of actions based on the values and on the historical information, executable code that compares the preliminary list to a list of safe actions, and executable code that removes from the preliminary list any action that is not on the list of safe actions to produce a safe list of actions that includes the determined action. The software may further include executable code that generates a preliminary list of actions based on the values and the historical information, executable code that determines a best action from the preliminary list, and executable code that sends a communication from the device to the health device directing performance of the best action.

BRIEF DESCRIPTION OF THE DRAWINGS

FIG. 3B is a block diagram illustrating at least a portion of a health data model, according to embodiments of the system described herein.

FIG. 5 is a flowchart illustrating remotely providing a health service to a recipient, according to embodiments of the system described herein.

FIG. 6 is a flowchart illustrating constructing a health data model, according to embodiments of the system described herein.

FIG. 7 is a flowchart illustrating preconfiguring an MLE, according to embodiments of the system described herein.

FIG. 8 is a flowchart illustrating configuring a mobile health device prior to delivering possession to a recipient, according to embodiments of the system described herein.

FIG. 9 is a flowchart illustrating authenticating a user of a mobile health device, according to embodiments of the system described herein.

FIG. 10 is a flowchart illustrating activating a mobile health device in response to detecting motion of the mobile health device, according to embodiments of the system described herein.

FIG. 11 is a flowchart illustrating reducing power consumption of a mobile health device based on detected temperature, according to embodiments of the system described herein.

DETAILED DESCRIPTION OF VARIOUS EMBODIMENTS

Figure 2D:
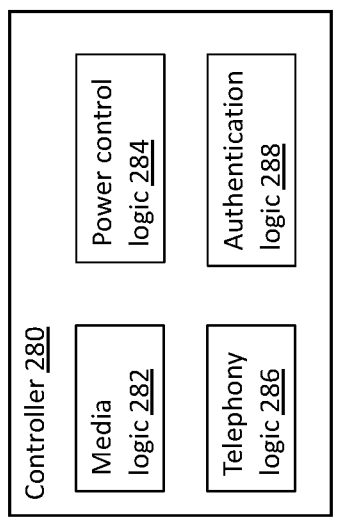
FIG. 2D is a block diagram illustrating an example of a controller of a health device, according to embodiments of the system described herein.

Traditional healthcare delivery is conducted through direct interactions with clinicians or other health care providers who analyze medical information of a patient, including historical information and currently detected information, and then, based on the analysis, perform procedures or prescribe other interventions such as medication and therapy. For acute problems like broken bones, this model of delivery can be efficient and effective. For long-term chronic medical conditions, direct interactions with medical specialists may be too costly and/or infrequent to adequately monitor and or treat such chronic conditions. Such chronic conditions may require more frequent monitoring and adjustments of treatment outside a physician's office hours.

More frequent monitoring (e.g., continuous monitoring) may be achieved by a patient or personal caregiver, independently from a trained practitioner, using a mobile device (e.g., including a medical sensor and/or other medical functionality) locally coupled to the patient and/or operated by the patient or the personal caregiver. For example, a CGM may be employed to continuously monitor blood glucose levels in a patient. A device (e.g., a mobile device with medical or other health functionality) may be deemed locally coupled to a person (e.g., a patient) if: the device itself, a portion thereof, or an accessory physically attached thereto (e.g., wire, a tube, a syringe, a catheter, a blood pressure cuff, blood pressure wrist monitor, other type of wrist monitor, patch, etc.) is in physical contact with the person's skin, is near enough to the person's body to detect a measurable value of a health metric (e.g., a physical property) of the person, is currently inserted in the patient's body, or resides within the person's body; and/or if the device is in direct wireless communication with an electromagnetic device (e.g., medical sensor) within the person's body, for example, a subcutaneous sensor of a CGM or pacemaker.

However, notwithstanding significant progress in the development of medical devices for monitoring health metrics, e.g., for outpatient services, such medical devices may lack the capability to wirelessly connect to a cloud service, much less a cloud service that provides real-time analysis of the patient's condition based at least in part on the detected values of remotely monitored health metrics.

Accordingly, it may be desirable to provide medical services that address these potential shortcomings.

Described herein are a system and techniques for providing remote health services (e.g., medical services) to a recipient of the health services (e.g., a patient). In some embodiments, the system described herein may include a network-connected mobile device (e.g., with health monitoring functionality; e.g., medical sensors) and cloud services configured for reliable data exchange and remote monitoring and analysis of a recipient's health metrics (e.g., blood pressure, blood glucose level, pulse and other metrics), which may enable providing health services remotely and in real time. Such remote health services may include determining a customized treatment for a recipient, for example, based on the recipient's profile and health history (including, e.g., medical history), including remotely monitored health metrics of the recipient.

The customized treatment may be determined by a trained practitioner, who analyzes a recipient profile and health history, including, for example, monitored health metrics, pharmaceutical usage, socio-economic factors and recipient feedback. The practitioner may analyze and reconcile information from these disparate sources and choose one or more interventions to recommend. These interventions may include, for example, direct medical or therapeutical procedures, other direct actions or adjustments to a recipient's care regimen or lifestyle that the recipient and/or a caregiver implements. Later, the practitioner may analyze the effects of those interventions, by again analyzing the recipient profile and health history, which now may include health metric measurements and recipient feedback occurring after the previously recommended interventions were performed. The practitioner's analysis may result in the practitioner adjusting the recommended interventions accordingly. This process may be performed iteratively over time.

This process including aggregation of recipient information, interpretation, intervention, and adjustment described above, performed iteratively, may be effective in treating the recipient, but it may not be cost effective to perform more than a few times per year. That is, the cost associated with employing the time and expertise of the trained practitioner to perform such a process more than a few times a year may be cost prohibitive to a recipient. Furthermore, depending on a practitioner's caseload, it may not be feasible for the practitioner to perform such a process more than just a few times per year while keeping up with the practitioner's caseload. Also, given the caseload of a practitioner, and practical time constraints, it may prove difficult for the practitioner to effectively digest all of the information available for aggregation and interpretation to determine and adjust interventions for the recipient.

Thus, it may be desirable to provide real-time remote health services (e.g., for a health condition for which one or more health metrics are remotely—and perhaps continuously—monitored), for example, in a manner that is reliable, time-efficient and cost-effective for recipients and/or practitioners.

The system and techniques described herein may provide remote health services, for example, in real time, based on values of health metrics monitored remotely, and in some embodiments, continuously, for a recipient. The system may include a mobile health device, for example, a mobile medical device (e.g., a glucometer), configured to continually monitor or intermittently detect values of one or more health metrics. A mobile health device may be configured for handheld operation and/or table-top operation, may be locally coupled to a recipient, and may include a health sensor (e.g., a medical sensor) that detects (e.g., monitors) values of one or more health metrics of the recipient, detecting such values continuously or intermittently (e.g., periodically or in response to user input). While embodiments of the system described herein are illustrated using a single health sensor, it should be appreciated that the invention is not so limited, as a health device may include multiple health sensors, and each health sensor may detect values for one or more health metrics.

The system described herein may include one or more servers remotely coupled to the mobile health device (e.g., over one or more communications networks) that are in communication with the health device and provide one or more health services (e.g., cloud services or cloud-based services) based at least in part on health metric values detected by the health device and transmitted to the remotely coupled servers. The one or more servers may implement a health services application (in any suitable combination of hardware, firmware and/or software) that analyzes recipient information, including a recipient's health history and detected health metric values, and determines interventions, which includes determining whether to intervene, and may include determining how and/or when to intervene. Determining interventions may include determining any of: whether it is necessary or desirable to perform one or more actions for the recipient; whether to communicate information (e.g., health information) to the recipient; the content of such information; and one or more characteristics of the communication of such information, as described in more detail elsewhere herein. A communication from a health services application to a health device as part of providing a health service, which may include specifying one or more actions corresponding to one or more interventions, may be referred to herein as a "health communication." It should be appreciated that some health communications may not be specific to the health of the recipient, but may be directed to a general engagement with the recipient or specific to the operation of the health device, as is described in more detail elsewhere herein.

If, as part of determining interventions, it is determined that it is desirable or necessary to perform one or more actions, the content of the health communication may specify the one or more actions and include an explanation of why the one or more actions should be performed. The health communication then may be communicated to the health device according to health communication characteristics determined for the health communication, as described in more detail elsewhere herein.

The health services application may be configured to analyze autonomously, at least in part, the recipient information to determine interventions, for example, using predefined rules and/or a machine learning engine (MLE). In some embodiments, in addition to, or as an alternative to, autonomously analyzing recipient information to determine interventions, the health services application may solicit and/or receive human input. For example, in some embodiments, at least part of the analysis and intervention determination may be performed by a trained practitioner. In some embodiments, the health services application may be configured to determine—based on recipient information, detected health metric values and rules corresponding to the health condition for which services are being provided—what one or more types of analysis (e.g., ruled-based, machine learning and/or human) are to be executed to determine interventions.

In some embodiments of the system described herein (e.g., embodiments in which machine learning is employed), as part of determining interventions, recipient information may be analyzed to determine a preliminary list of one or more actions to instruct or recommend performing as part of performing the service. This list may be filtered (e.g., using safety rules and/or a list of safe or unsafe action) to remove one or more actions that are deemed unsafe (e.g., clinically unsafe). Employing machine learning to autonomously or semi-autonomously determine interventions may be more dynamic and flexible than employing purely rules-based analysis, but the results also may be more unpredictable than those from rules-based analysis. While such unpredictability may be acceptable for some fields (e.g., marketing, games), it may not be acceptable for determining health interventions, especially for medical interventions. Accordingly, for safety reasons, it may be desirable to use safety rules and/or a list of safe or unsafe actions to filter a preliminary list of actions provided by the machine learning. In some embodiments, the filtering may be applied before generating the preliminary list (e.g., using machine learning); for example, to rule out the possibility of any potentially dangerous actions being produced from the analysis.

In addition to filtering the preliminary list, the preliminary list may be ranked, for example, before or after the preliminary list has been filtered by application of safety rules, and the ranked list may be analyzed to determine a best one or more actions on the ranked list—i.e., the one or more actions deemed best-suited to treat the health condition of the recipient based at least in part on the recipient information. The one or more actions that remain after the filtering and selecting described above (sometimes referred to herein as the definitive actions(s)) may be communicated in one or more health communications to the health device, which then may communicate (e.g., visually and/or audially) the one or more definitive actions to the user of the health device and/or may autonomously implement one or more of the definitive actions.

The health device may include one or more components to enable audial, visual and written correspondence between a user of the health device (e.g., recipient or caregiver) and the one or more remote devices and/or practitioners, for example, in real-time, as described in more detail elsewhere herein.

In some embodiments, the health device may be configured to control power consumed by, and/or the thermal output of, the health device based on detected temperatures within, or proximate to, certain regions of the health device and/or based on detected movement of the health device or a component thereof, as described in more detail elsewhere herein.

In some embodiments, the health device may be pre-configured (e.g., customized) for a recipient, before delivery to the recipient, based on information about the recipient, which may include health information about the recipient. Such information, for example, in the form of a recipient profile, may be accessed in response to a purchase and/or ordering of the health device by, or on behalf of, the recipient. Upon delivery, the user may be authenticated based on the recipient information, for example, using multi-factor authentication, as described in more detail herein.

In some embodiments, a health services application (e.g., implemented on one or more servers) may be configured to determine—e.g., based on previous recipient information provided to a health services application and/or previous health metric values detected from a health device locally coupled to the recipient—when detected health metric values constitute an irregularity (i.e., an anomaly). For example, analysis of the most recently detected health metric values may determine that the most recent values were detected from a person other than the recipient, or that such values represent a significant and potentially dangerous change in a recipient's condition. In response to detecting an irregularity, a notification may be sent to one or more entities, for example, a responsible health professional, the health device (e.g., as part of a health communication sent to the user of the health device) and/or to another known device (e.g., cell phone, home phone, laptop) of the recipient or a caregiver.

Figure 1:
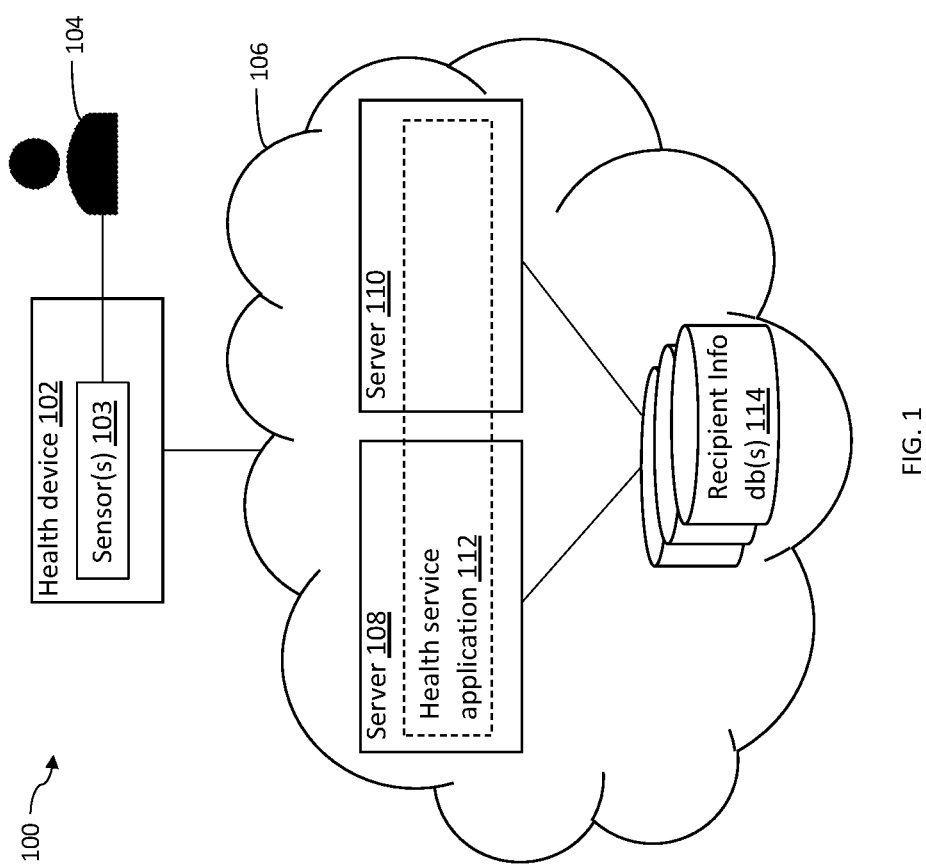
FIG. 1 is a block diagram illustrating a system for remotely providing a health service to a recipient, according to embodiments of the system described herein.

Illustrative embodiments of the system described herein will now be described in relation to the drawings. It should be appreciated that the system described herein is not limited to the following illustrative embodiments, as other embodiments, for example, variations of the following illustrative embodiments, are possible, and intended to fall within the scope of the invention FIG. 1 is a block diagram illustrating a system 100 for remotely providing a health service to a recipient, according to embodiments of the system described herein. Other embodiments of a system for remotely providing a health service to a recipient, for example, variations of the system 100, are possible and are intended to fall within the scope of the invention.

The system 100 may include any of: a health device (e.g., mobile health device 102), which may be locally coupled to a recipient (e.g., a patient) 104; one or more servers 108, 110 implementing a health services application 112; one or more recipient information databases 114; other components (not shown); or any suitable combination of the foregoing. The servers 108, 110 and recipient info dbs 114 may reside on a network 106. The servers 108, 110 may host health services application 112, and may be considered remote with respect to the health device 102 (and thus the recipient 104) in the sense that the servers 108, 110 communicate with the health device 102 over one or more network links (other than a direct NFC link, Blue Tooth link or the like) of network 106. For example, the mobile health device 102 may be used at the home of the recipient 104, whereas the servers 108, 110 may reside at a medical center or the like, or a separately located data center thereof. The servers 108, 110 may be part of a server cluster or other logical and/or physical grouping of servers, and may include only one server or more than two servers.

The network 106 may include any one or more of a variety of communication media, switches and other components, including, for example: a repeater, a multiplexer or even a satellite. Each communication medium may be any of a variety of communication media including, but not limited to: a bus, a wire, an optical fiber, air and/or other type of communication medium. The network 106 may include at least a portion of the Internet, a satellite-based network, a mobile or land-based telephony network, a proprietary intranet, another type of network, or any suitable combination of the foregoing. Components of the network 106 or components connected thereto may be configured to communicate in accordance with any of a plurality of technologies, including, for example: GSM (e.g., 2G, 3G, LTE, 5G), TCP/IP, UDP, Ethernet, GIGE (Gigabit Ethernet), other Local Area Network (LAN) protocols, Wide Area Network (WAN) protocols, file transfer protocols, OSI protocols, SCSI, ESCON, Fibre Channel (FC), iSCSI, FCoE, NVMe over Fabric (NVMf); other technologies, or any suitable combinations of the foregoing, each of which may have one or more associated standard specifications.

The mobile health device 102 may include one or more health sensors 103 to monitor (in some embodiments using one or more coupled accessories) values of one or more health metrics of the recipient 104 such as, for example, blood glucose level and blood pressure, e.g., as described in more detail elsewhere herein. The one or more health sensors 103 and accessories thereto may include any of: a blood glucose meter, blood pressure monitors (e.g., including a wrist monitor and/or a cuff), an electronic scale, sleep monitor, fitness activity tracker, thermometer, catheter, subcutaneous sensor, syringe, tube, wire, stethoscope, electrode (e.g., an EKG electrode), patch, other health sensors and/or accessories, or any suitable combination of the foregoing.

The health device 102 may be configured (e.g., with one or more network interface components) to communicate detected values of health care metrics to health services application 112. The health services application 112 may be configured to analyze the received health metric values along with other recipient information from recipient information dbs 114 to determine interventions, as described in more detail elsewhere herein. The health services application 112 may communicate intervention information in one or more health communications to the health device 102. Each health communication may describe one or more definitive actions to be performed by the recipient 104 or a caregiver of the recipient and/or one or more definitive actions to be performed or controlled autonomously by the health device 102.

The health device 102 may be configured with one or more audial, visual and/or tactile output technologies to communicate health communications and/or other information to a user of the health device 102 (e.g., the recipient or caregiver). The health device 102 also may be configured with one or more audial, visual and tactile input technologies to allow the user of the health device 102 to input information associated with a health service, e.g., to be communicated to the health services application 112. The health device 102 further may be configured to implement one or more conversion technologies for converting information from one form of media and/or format thereof (e.g., audio, video or text encoded in accordance with a particular technology standard) to another form of media and/or format thereof. One or more of these conversion technologies may be applied to information received from the user of the health device; e.g., to be sent to the health services application 112; and one or more of these conversion technologies may be applied to information received from the health services application 112 or another remote source; e.g., to be presented to the user of the health device. Audial, visual and tactile input and output technologies, and conversions therebetween, are described in more detail elsewhere herein.

The health device 102 may be pre-configured (i.e., before delivery to the recipient or caregiver thereof), authenticated and activated as described in more detail elsewhere herein. Further, power consumption and thermal output of the health device 102 may be controlled as described in more detail elsewhere herein. The health device 102 may be implemented as health device 200 described in relation to FIGS. 2A-2D, which will now be described.

Figure 2A:
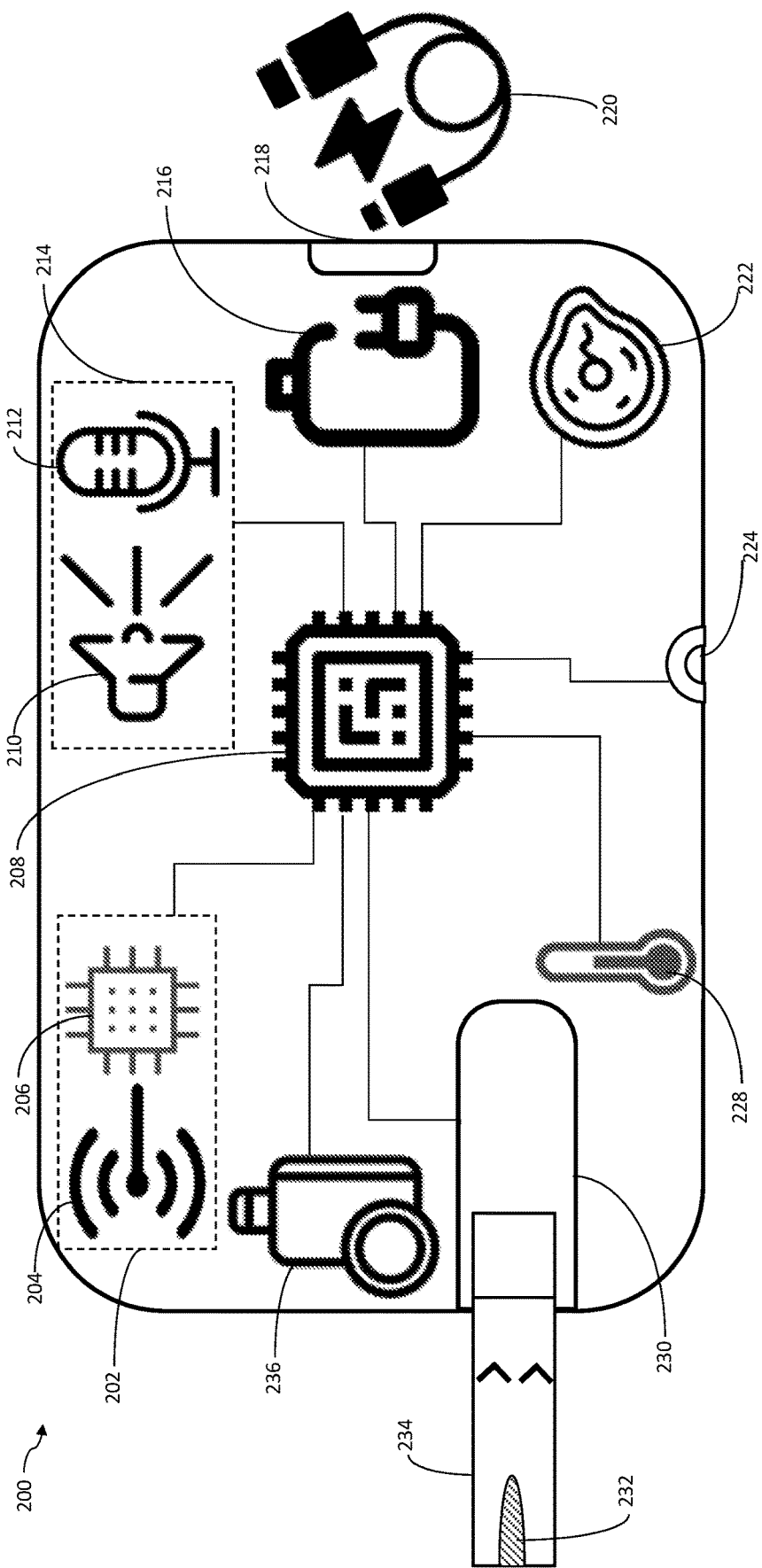
FIG. 2A is a block diagram illustrating a schematic representation of a mobile health device, according to embodiments of the system described herein.

FIG. 2A is a block diagram illustrating a schematic representation of a mobile health device 200, according to embodiments of the system described herein. Other embodiments of a mobile health device, for example, variations of the mobile health device 200, are possible and are intended to fall within the scope of the invention. FIG. 2A includes various icons to illustrate a certain functionality and/or capabilities, but it should be appreciated that such icons do not necessarily reflect the physical attributes of the underlying components implementing the functionality or capability.

The mobile health device 200 may be physically configured for desktop or handheld use, and may have a form factor at least similar to that of an electronic tablet, notepad, personal digital assistant (PDA) or smart phone, as well as other form factors. The mobile health device 200 may include any of: wireless connectivity components 202, which may include a wireless antenna 204 and a wireless chipset 206; a controller (e.g., main processor) 208; audio components 214, which may include a speaker 210 and a microphone 212; a rechargeable battery 216; a charger plug 218; a charging cable 220; one or more motion sensors 222; an external plug 224; one or more temperature sensors 228; a reader module 230; an external health sensor (e.g., test strip 234), including a test sample area 232; camera components 236; a display screen (not shown); other components; and any suitable combination of the foregoing.

The wireless connectivity component 202 may be configured to provide wireless communication between the mobile health device 200 and other devices, for example, the servers 108, 110, to communicate with the health services application 112. The wireless chipset 206 may be configured (e.g., physically, electronically programmed and/or programmed with firmware and/or software) to control (perhaps in combination with, or under direction of, the controller 208) processing of wireless communication sent to, and received from, other devices through the antenna 204. The wireless connectivity component 202 also may be configured to exchange information with an accessory of a health device, for example, a wrist monitor, patch or subcutaneous component.

The audio components 214 may be configured to receive and transmit audio signals, for example, using the microphone 212 and the speaker 210, respectively. The controller 208 may include logic to control and/or process audio communications to and from the audio components 214, for example, audio content in health communications received via the wireless connectivity components 202, or converted from text content of such health communications, and bound for the audio component 214. The one or more motion sensors 222 may be configured to detect motion of the health device 200, and each motion sensor may be any of a variety of motion sensors configured to detect different types of motion, including, for example, a gyroscope, magnetometer, accelerometer, or a GPS system. Each of the one or more temperature sensors 228 may be any of a variety of types of temperature sensor configured to detect a temperature in one or more regions internal and/or external to the health device 200.

In the illustrative example of FIG. 2A, the reader module 230 may be a glucose test strip reader configured to receive the test strip 234, where the test sample area 232 is configured to receive blood of a user. Any of a variety of other readers that can be accommodated on the health device 200 may be included therein, in addition to, or in place of, the reader module 230.

In some embodiments, the health device 200 may be configured to include one or more thermal buffers (e.g., air/space, insulating material) between any one or more health sensors (e.g., the reader module 230) and one or more other components of the health device 200. Including the buffers may be done to thermally insulate a health sensor from the one or more other components so that heat generated by operation of the other components does not affect operation of the health sensor, for example, the accuracy of the values detected thereby.

The external plug 224 may be configured to receive a connector (e.g., cable, wire) of any of a variety of types of devices, including accessories to the health device 200. For example, a blood pressure cuff may be connected to the health device 200 through the external plug 224, for example, to convey information from the blood pressure cuff (or other accessory) to the controller 208 and/or instructions from the controller 208 to the blood pressure cuff (or other accessory). The camera component 236 may include a camera and associated logic for capturing video and/or still images, conveying such video and/or images to the controller 208 (or other components) and/or receiving information (e.g., instructions) from the controller 208 (or other components(s) of the system), for example, in connection with providing health services as described in more detail elsewhere herein.

The controller 208 may include memory and one or more CPU cores and/or other computational components, on which any of a variety of firmware, operating systems (OSs) and other software may execute to implement functions of a health device described herein. The controller 208 may be coupled with, and configured to control, one or more other components of the health device 200, for example, any of the components described herein. The controller 208 may include one or more sub-components (e.g., logic) configured to perform one or more specific functions, for example, one or more methods, steps or sub-portions thereof described in more detail elsewhere herein.

Figure 2C:
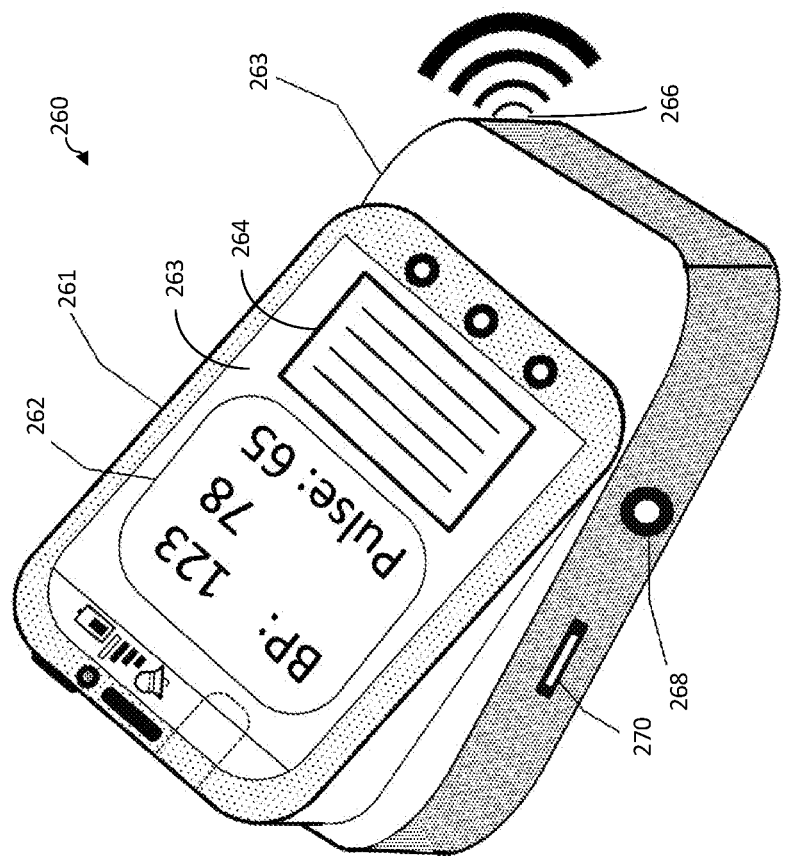
FIG. 2C is a perspective view of a mobile health device mounted on a base station for the health device, according to embodiments of the system described herein.
Figure 2B:
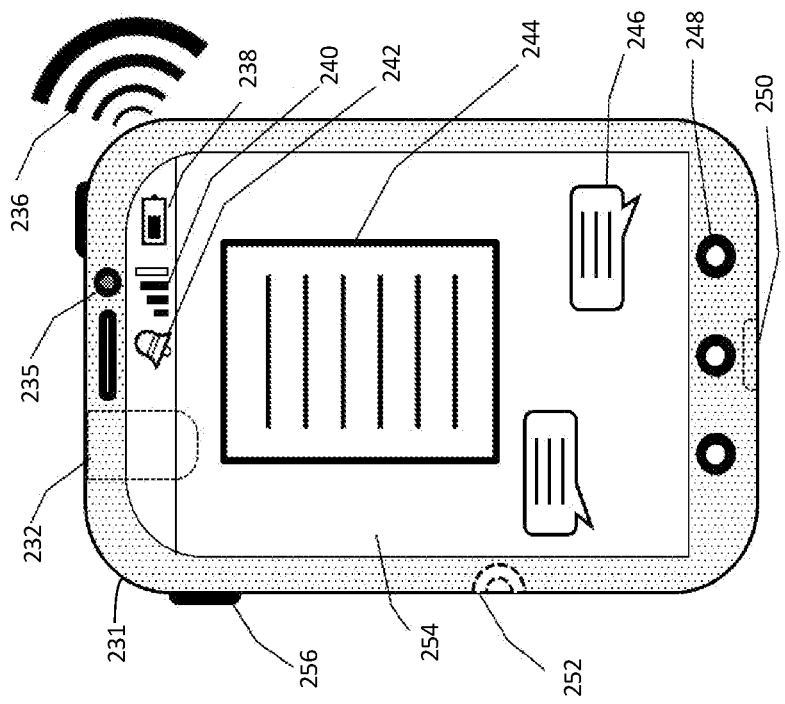
FIG. 2B is a plan view of a mobile health device, according to embodiments of the system described herein.

FIG. 2B is a plan view of a mobile health device 231 (e.g., the health device 200), according to embodiments of the system described herein. Other embodiments of a mobile health device, for example, variations of the mobile health device 231, are possible and are intended to fall within the scope of the invention. FIG. 2B includes various icons to illustrate certain functionality and/or capabilities, but it should be appreciated that such icons do not necessarily reflect the physical attributes of the underlying components implementing the functionality or capability.

The mobile health device 231 may include any of: a reader module 232 (e.g., the reader module 230); a camera component 235 (e.g., the camera component 236); wireless connectivity components 236 (e.g., the wireless connectivity components 202); a battery indicator 238; a wireless signal indicator 240; an alarm indicator 242; health communication content 244 (e.g., instructions); a notification 246; a control button 248; a charger plug 250; an external plug 252 (e.g., the external plug 224); a display screen 254; and a side button 256.

The alarm indicator 242 may be controlled (e.g., by the controller 208) to visually indicate an alarm, for example, in response to a health communication, as described in more detail elsewhere herein. The display screen 254 may be controlled (e.g., by the controller 208) to display any of a variety of information in connection with providing a health service, for example, the health communication content 244 and the notification 246. The control button 248 and the side button 256 may be configured to provide any of a variety of functionality in response to being pressed once, pressed multiple times in rapid succession and/or held, including, for example, screen and control navigation, power on/off, component or functionality activation/deactivation, volume control, brightness control, health service functionality, other functionality or any suitable combination of the foregoing.

In some embodiments, the mobile health device 200 may be configured to be capable of being docked on a base station, e.g., for charging and/or desktop use, for example, as illustrated in FIG. 2C. FIG. 2C is a perspective view 260 of a mobile health device 261 (e.g., the mobile device 200) mounted on a base station 263, according to embodiments of the system described herein. Other embodiments of a mobile health device mounted on a base station for the health device, for example, variations of the mobile health device 261 and base station 263, are possible and are intended to fall within the scope of the invention. FIG. 2C includes various icons to illustrate certain functionality and/or capabilities, but it should be appreciated that such icons do not necessarily reflect the physical attributes of the underlying components implementing the functionality or capability.

The mobile health device 261 may be the same as or similar to the mobile health device 231, and may include any of the components thereof. For example, the mobile health device 261 may include a screen 263 for displaying health communication content 262, 264. The base station 263 may include any of: wireless connectivity components 266; and external plugs 268, 270 for externally coupled accessories, power and/or charging.

FIG. 2D is a block diagram illustrating a controller 280 (e.g., the controller 208) of a health device (e.g., the health device 200), according to embodiments of the system described herein. Other embodiments of a controller of a health device, for example, variations of the controller 280, are possible and are intended to fall within the scope of the invention. The controller 280 may include any of: media logic 282; power control logic 284; telephony logic 286; authentication logic 288; other logic; or any suitable combination of the foregoing.

The media logic 282 may include any of: audial and/or visual encoding logic for encoding audio, video and still images captured by a microphone or other audio capture device (e.g., the speaker 212) and/or camera (e.g., the camera 236) or other video/image capture devices of the health device; audial and visual decoding logic for decoding audio, video and still images for rendering on a speaker (e.g., the speaker 210) and/or display screen (e.g., the display screen 254) on the health device; media type conversion logic for converting between types of media (e.g., text-to-speech converter, speech-to-text conversion); and media format converting logic for converting from one media format to another; for example, from a serialized video format to a format for displaying on a display screen. The media logic 282 may be configured to control the audio components 214 and/or the camera components 236, and may be utilized to perform one or more methods, steps, or portions thereof described herein, in relation to using media (e.g., audial data, visual data or textual data) as part of providing a health service.

The power control logic 284 may be configured to control power consumption and/or thermal output of one or more components, for example, as described in more detail elsewhere herein. The telephony logic 286 may be configured to perform one or telephony functions, for example, in connection with exchanging communications between the health device and a health services application, as described in more detail elsewhere herein. The authentication logic 288 may be configured to authenticate a user (e.g., a recipient) of the health device, for example, as described in more detail elsewhere herein.

Figure 3A:
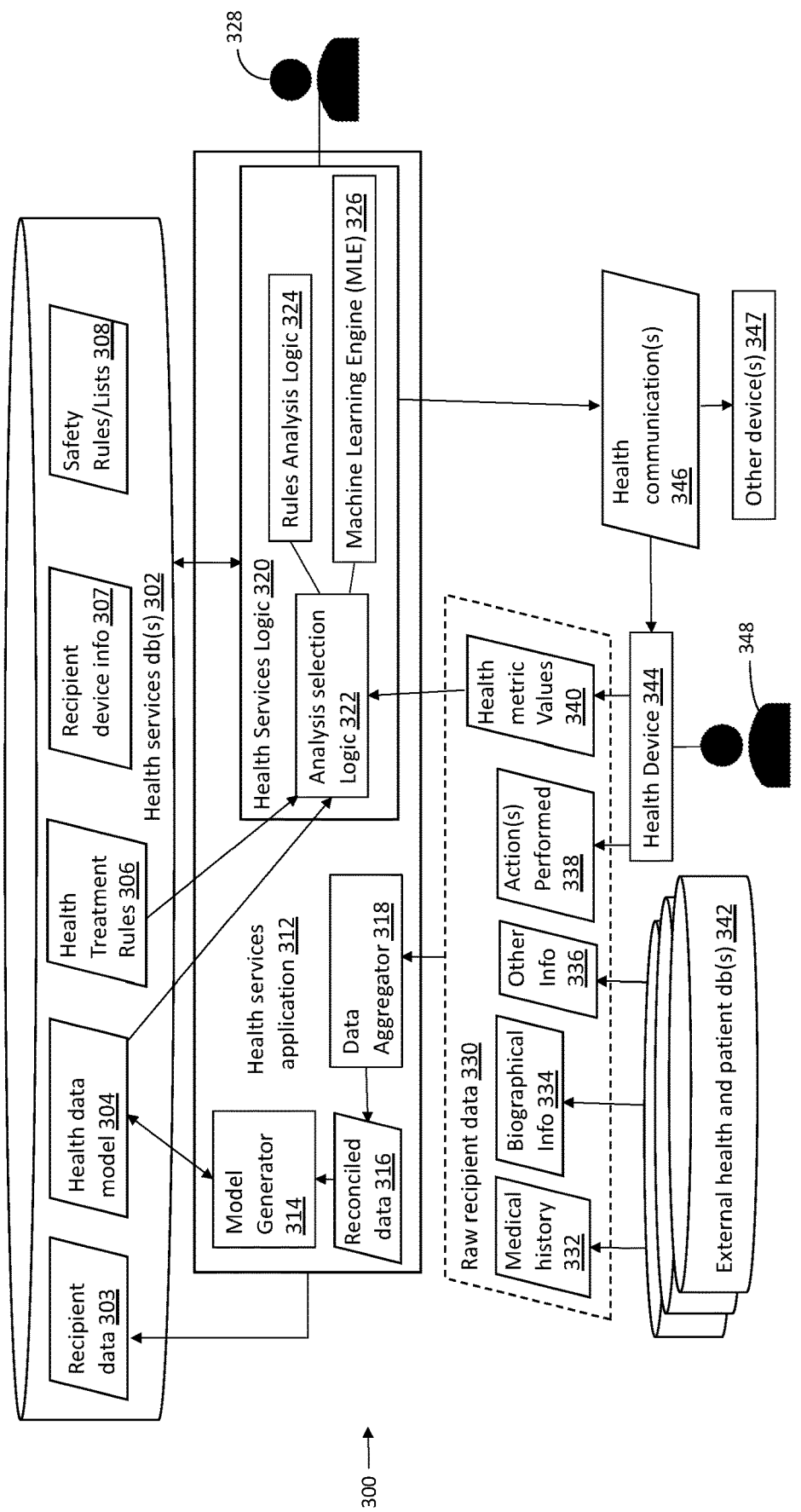
FIG. 3A is a data flow diagram illustrating a system for remotely providing a health service to a recipient, according to embodiments of the system described herein.

FIG. 3A is a data flow diagram illustrating a system 300 for remotely providing a health service to a recipient, according to embodiments of the system described herein. Other embodiments of a system for remotely providing a health service to a recipient, for example, variations of the system 300, are possible and are intended to fall within the scope of the invention. The system 300 may include any of: a health service database(s) 302 (including, e.g., the recipient information db(s) 114); a health services application 312 (e.g., the health services application 112); external health and recipient databases (dbs) 342; a health device 344 (e.g., the health device 102); other devices 347; other components; or any suitable combination of the foregoing.

The health services application 312 may include a data aggregator 318 that: receives raw recipient data 330 associated with a recipient 348, a health condition and/or a health service; aggregates the received data; and reconciles the aggregated data to produce reconciled data 316. The raw recipient data 330 may include any of: a health history 332 of the recipient 348; biographical data 334 about the recipient 348; health metric values 340 of the recipient 348 detected by the health device 344; information concerning actions performed by the recipient 348 and/or the health device 344 (e.g., in response to one or more health communications 346 communicated by health services application 312); and other information 336. The health history 332; biographical info 334 and other information 336 may be received from one or more health and/or recipient databases 342, which may be external databases controlled or maintained by other entities.

The health services application 312 may include a model generator 314 that receives the reconciled data and generates a health data model 304, which the health services application 312 may store in the health services db(s) 302. The health services application 312 also may store recipient data 303 in the health services db(s) 302. The recipient data 303 may include the raw recipient data 330 and/or data derived therefrom, e.g., the reconciled data 316 or a partially reconciled version of the raw recipient data 330.

FIG. 3B is a block diagram illustrating a data structure 350 that may be at least a portion of the health data model 304, according to embodiments of the system described herein. Other embodiments of a data structure for a portion of a health data model, for example, variations of the data structure 350, are possible and are intended to fall within the scope of the invention. The data structure 350 may include a plurality of entries (e.g., rows) 360*a-c*, each entry corresponding to a set of one or more pieces of information corresponding to a time (or period of time) specified in time column 352, for example, the time at which such information was recorded or obtained. It should be appreciated that more or less than three entries, as illustrated in FIG. 3B, may be included in the data structure 350. For each entry, the data set may include one or more pieces of data, each piece of data being a value of a parameter for a particular parameter column, e.g., one of parameter columns 354, 356, and 358. Such parameters may include parameters for demographic information about the patient (e.g., age, weight, gender), health metric values (e.g., any of those described herein), health device information (e.g., last time used), actions performed by the user, and other information, interventions determined for the recipient, health communications communicated to a mobile health device, actions taken by the recipient, the timing, duration and expiration of interventions and/or actions, other parameters or any suitable combination of the foregoing.

A first entry 360*a* may represent a most recent time or period of time, and the remaining entries may represent older times or periods of time. In some embodiments, the first entry may be considered the current state of health of the recipient, and the remaining entries the historical health data for the patient, and collectively all of the entries may be considered to represent a chronology of the recipient's state of health. In some embodiments, a value is not included for every parameter column. For example, the raw recipient data 330 may have included information about an action performed, but not include any health metric values, in which case a resulting entry in the data structure 350 may not include any health metric values. In some embodiments, each entry in the data structure includes a value for every parameter. For example, for some parameters, even if a new value has not been received as part of the raw recipient data 330, a default value may be included for the entry for the parameter; e.g., a most recent value detected for the parameter. For example, if the raw recipient data 330 includes information about an action performed, but does not include any health metric values, a most recent value (e.g., average blood pressure) may be used as a default value for the entry.

In some embodiments, one or more parameters have a value that never changes or seldom changes (e.g., gender) or can automatically be determined (e.g., age), in which case the value may be the same in each entry of the data structure 350 and/or a header may be provided that defines the values of such parameters.

Is should be appreciated that, although data structure 350 is illustrated as a table, any of a variety of other types of data structures may be used, including an object-oriented data structure, linked list, other type of data structure or suitable combination of the foregoing, and there may be more than one such data structure. Further, one or more indexes may be created for any of the columns/fields or other data elements of such data structures (e.g., data structure 350).

It should be appreciated that the health services db(s) 302 may include multiple ones of the health data model 304 (e.g., including the data structure 350 or a portion thereof), each health data model corresponding to a specific recipient. Further, the health services db(s) may include data structures that include information resulting from combining information described above from multiple recipients.

Returning to FIG. 3A, the health service db 302 also may include health treatment rules 306, recipient device information 307, safety rules and/or safety lists (e.g., a safe action list, described in more detail elsewhere herein) 308, described in more detail elsewhere herein. The recipient device information 307 may include information about one or more health devices of the patient including, for example: model, serial number, operating system and version, firmware and version, other software and versions, owner or lessee, date of purchase, features, technical specifications, current and past locations, etc. It should be appreciated that the health services db(s) 302 may include recipient device information for multiple recipients.

The health treatment rules 306 and the safety rules/lists 308 may be defined (at least initially) by a human and/or by automated processes. In some embodiments, each of the sets of rules/lists 306, 308 may remain static until modified by a human or automated process. The health treatment rules 306 and the safety rules/lists 308 may not be specific to any one recipient, but rather, applied for multiple (e.g., all known) recipients. In some embodiments, a machine learning engine (MLE), after being initially configured, may autonomously update one or more of these rule sets/lists based on iterative calculations made each time the health metric values 340 are received and processed by the health services logic 320. Furthermore, the data aggregator 318 and the model generator 314 may update the reconciled data 316, the recipient data 303 and/or the health data model(s) 304 from time to time, in response to new raw recipient data. Furthermore, the MLE 326 may be configured to update functionality of the MLE 326 (e.g., weights for its layers and/or gates if it is an artificial neural network) and/or the health treatment rules 306 based on new raw recipient data, for example, as described in more detail elsewhere herein.

The health services logic 320 may include analysis selection logic 322 that receives the health metric values 340 from the health device 344 for a recipient, and accesses the health data model 304, the health treatment rules 306, and/or the recipient data 303, and perhaps other information in the health service db 302. The health services logic 320 may be configured to determine, based on the health metric values 340 and information accessed from health service db 302, what type of analysis to perform to determine interventions. The type of analysis may include applying predefined rules-based logic, machine learning or human analysis. Based on the determination of analysis type, the health services logic 320 may control rules analysis logic 324 or the MLE 326 to determine interventions based on the health metric values 322 and information from the health services db(s) 302; or the health services logic 320 may prompt (e.g., via a user interface) a trained practitioner 328 (e.g., doctor, nurse, paramedic, physical trainer, health coach, etc.) to analyze received values and available information to determine interventions.

It should be appreciated that the qualifications for a trained practitioner will depend on the health condition being serviced (e.g., treated) and perhaps contractual relationships between the recipient and entities or organizations (e.g., medical center, clinic, insurance company, university, rehabilitation center, wellness center, physical trainer, etc.) with which the practitioner and/or recipient is affiliated.

The analysis type selected by the analysis selection logic may depend on a variety of factors, including, for example: the one or more health conditions being serviced; the health history of the recipient, generally and with respect to the one or more health conditions, including any recent trends in the health history; demographic information about the recipient, including, age, gender, race, residential location; most recent health metric values, contractual obligations, etc. The factors may be gleaned from the health metric values 340, the health data model 304, the recipient data 303 and/or the health treatment rules 306. It should be appreciated that a different type of analysis may be selected at different times for a same recipient and health condition. For example, if the health metric values 340, the health data model 304, the recipient data 303 and/or the health treatment rules 306 reflect a clearly typical and/or benign condition of the recipient (e.g., typical blood glucose levels for the recipient), the rules analysis logic 324 or the MLE 326 may be selected and engaged. However, if the health metric values 340 and information from the health service db 302 reflect a possibly significant change in a condition of the recipient, such as a severe condition and/or an irregularity (e.g., a spike in the blood glucose level of the recipient), human evaluation by a trained practitioner (e.g., a medical doctor) may be selected, and the practitioner 328 may be engaged. For example, if the health metric values reflect a serious enough (or potentially serious enough) medical condition, it may be desirable to contact a physician or other doctor rather than relying on an autonomous system.

It should be appreciated that at least some of the logic involved in selecting the analysis type and in determining interventions may be codified within information included in the health service db 302, e.g., in the data model 304, and the health treatment rules 306, the safety rules/lists 308

The health services logic 320, more specifically, the rule analysis logic 324 and/or the MLE 326, and/or the trained practitioner 328 may determine interventions based on the health metric values 322 and information from the health services db(s) 302; and may produce one or more of the health communications 346 based on determined intervention(s) that are sent to the health device 344 and/or one or more of the other devices 347 (e.g., a mobile phone, laptop computer or other device of a recipient). Determining intervention(s) may include determining a timing and/or expiration of one or more actions to perform for the intervention. For example, it may be determined that a patient should take a medication, but only if the medication is taken between 8:00 pm and 10:00 pm, an estimated time approaching a bedtime of a patient. Thus, the selected component(s) of health services logic 320 and/or the practitioner 328 may determine a timing of 8:00 pm to send a health communications to display a message to the patient and an expiration of 10:00 of the message. Thus, the health communication 346 may be sent at 8:00 pm, causing a message to be displayed on a screen of the health device instructing the patient to take the medication, until 10:00 pm, at which time the message may stop displaying, and perhaps a new message is displayed instructing the patient to take the medication when the patient wakes up in the morning.

The health services logic 320 may be configured to record information associated with an invention determination, including whether it was determined that an intervention (including a communication and/or one or more actions) will occur, and if so, the determined content, timing (if any), expiration (if any); characteristics of the health communications, and other contextual information associated with the intervention, including the value of one or more state variables and health information parameters that influenced the intervention determination. Such information may be recorded in the health services db(s) 302, including, for example, as part of the data model 304 and/or the recipient data 303.

The health communication(s) 346 may include content specifying one or more actions for the health device and/or recipient (or caregiver) to undertake, timing and expiration for the one or more actions, and values for health communication characteristics, described below.

Figure 4:
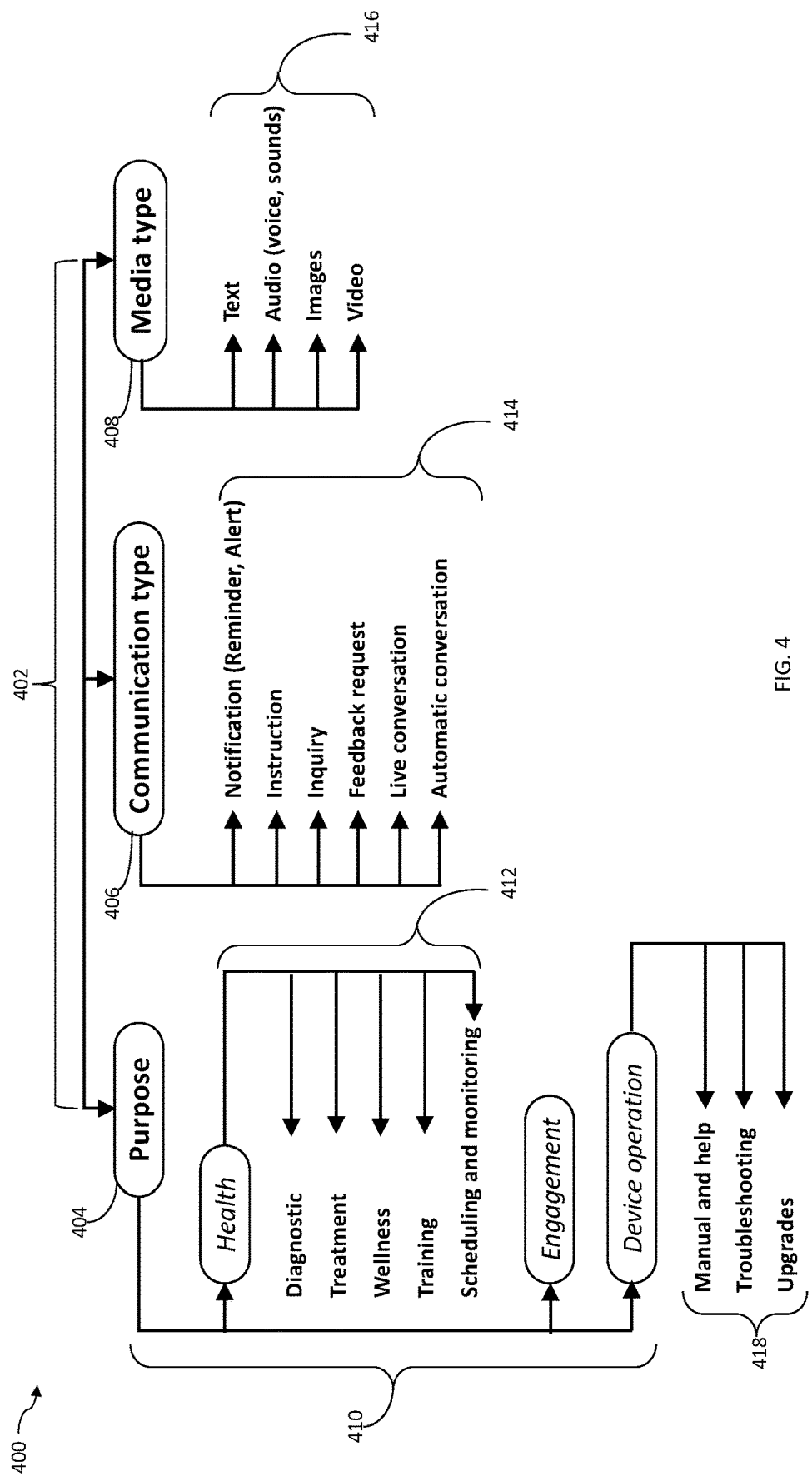
FIG. 4 is a diagram illustrating health communication characteristics, according to embodiments of the system described herein.

FIG. 4 is a diagram illustrating health communication characteristics 400, according to embodiments of the system described herein. Other embodiments of health communication characteristics, for example, variations of the characteristics 400, are possible and are intended to fall within the scope of the invention. The health communication characteristics may be stored in one or more data structures and may be codes in software and/or firmware.

The characteristics 400 of a health communication may include any of: purpose 404; communication type 406; media type 408; intervention analysis type (not shown); other characteristics; and any suitable combination of the foregoing. The purpose characteristic 404 may specify a purpose for the health communication. One of a plurality of purpose characteristic values 410 may include, for example, "health," "engagement" and "device operation."

A purpose characteristic value 410 of "health" may indicate that the purpose of a health communication is specific to the health of the recipient for whom the communication is sent. A purpose characteristic value 410 of "engagement" may indicate that a health communication is for general engagement of the recipient, as opposed to being specific to a health condition or the health device itself. For example, the health services application 312 may be configured to determine when there has been a long period of inactivity and may send a health communication to simply check-in on the general status of the recipient—e.g., ask why the recipient has not used the device yet, or has not used the device in some time, or confirm the recipient is still reading or hearing communications and/or still using the health device.

A purpose characteristic value 410 of "device operation" may indicate that a health communication is specific to the functioning of the health device, and may include an additional sub-value from among device-functioning sub-values 418, e.g., "manual and help," "troubleshooting" and "upgrades." For example, a device-functioning sub-value of "manual and help" may indicate that the purpose of a health communication is to provide device operation help or user-manual information to the recipient. A device-functioning sub-value of "troubleshooting" may indicate that the purpose of a health communication is to provide technical troubleshooting for an operational problem the recipient is having with the health device. A device-functioning sub-value of "upgrade" may indicate that the purpose of a health communication is to provide a software or firmware upgrade for the health device.

A plurality of communication type characteristic values 414 may specify a type of a health communication, for example, a notification (e.g., reminder, alert), instruction, inquiry, feedback request, live conversation, and automatic conversation. A notification type of communication may specify a reminder, alert or other type of notification for a recipient; for example, a reminder to take a medication or exercise, or an alert that blood pressure is trending higher and approaching dangerous levels. An instruction type of communication may specify an instruction for a recipient, for example, to take insulin because most recent blood glucose measurements were too low or too high, or to take photos or videos of a part of the recipient's body, food a recipient has been, is, or will be eating, or a document (e.g., a paper drug prescription), medication label, etc.

An inquiry type of communication may ask questions to the recipient, for example, about how they feel, recent activity or how closely they have been following a prescribed treatment. A feedback request type of communication may solicit feedback from the recipient following an intervention action. A live conversation type of communication may provide a most recent response from a practitioner as part of an ongoing conversation with the recipient; whereas an automatic conversation type of communication may provide a most recent automated response (e.g., generated by the rules analysis logic 324 or the MLE 326); e.g., from a chatbot, as part of an ongoing conversation with the recipient.

Accordingly, the communication type characteristic values 414 may include, for example, values of "notification", "instruction," "inquiry," "feedback request," "live conversation," "automatic conversation" or other communication types.

A plurality of media type characteristic values 416 may specify the type of media used to convey a health communication to a health device, for example, text, audio (e.g., voice, sounds), images, video, or a viable combination of one of the foregoing. Accordingly, the media type characteristic values 416 may include, for example, values of "text," "audio," "images," "video," or any suitable combination of the foregoing.

As noted above, the characteristics 400 of a health communication may include an intervention analysis type (not shown). The intervention analysis type may specify the type of intervention analysis applied (e.g., by the health services logic 320 of the health services application 312) that resulted in a health communication, or more specifically, the one or more interventions specified in the health communication. Values of an intervention analysis type may include, for example, rules-based analysis, MLE, human analysis, another analysis type, or any combination of the foregoing.

The health services logic 320 (e.g., the rule analysis logic 324 and/or the MLE 326) and/or the practitioner 328 may be configured to determine values for the health communication characteristics based on information obtained from the health services db(s) 302 and the health metric value(s) 340. For example, MLE analysis may determine that a health communication has a purpose of "treatment," a communication type of "instructions" and a media type of "audio;" i.e., that a health communication should be sent to the health device including an instruction for treatment in the form of audio recorded by a practitioner, which may be played as speech on the speaker of the health device and/or converted to text and displayed on a screen of the health device. As another example, a rules-based analysis may determine that a health communication has a purpose of "diagnosis," a communication type of "notification" and a media type of "text"; i.e., that a health communication should be sent to the health device including a notification of a diagnosis in the form of text, which may be displayed on a screen of the health device and/or played as speech on the speaker of the health device.

It should be appreciated that the decision of whether to convert audio content of a health communication to text and display it on a screen of the health device, or conversely to convert text to speech and play on a speaker of a health device, may be controlled by a user of the health device (e.g., the recipient). For example, the user may control whether the media format is converted using a graphical user interface presented on the health device and/or voice or tactile input of the health device. In some embodiments, the manner in which content is presented to a user is controlled by one or two parameters that may be pre-configured as part of the pre-configuration process described in more detail elsewhere herein. In some embodiments, the health communication itself may specify what media form the content is to be conveyed from the health device to the user, which may be different than the form in which the content is encoded and transmitted to the health device. For example, there may be separate health communication types for: media type for transmission to the health device; and media type for communicating from the health device to the user, and the health services logic 320 may be configured to set such values based on information obtained from the health services db(s) 302 and the health metric value(s) 340. In some embodiments, values for conveying content from the health device to the user set during pre-configuration may be overridden by the values specified in a health communication or by the user of the health device; and values specified in a health communication may be overridden by values entered by a user of the device.

The characteristics 400, potential values thereof, and actual values attributed to a health communication (e.g., one of the health communication(s) 346) transmitted from a health application service (e.g., the health services application 312) to a health device (e.g., the health device 344) may be recorded, for example, in the health services db(s) 302.

FIG. 5 is a flow diagram 500 illustrating remotely providing a health service to a recipient, according to embodiments of the system described herein. Other embodiments of remotely providing a health service to a recipient, for example, variations of processing illustrated by the flow diagram 500, are possible and are intended to fall within the scope of the invention.

In a step 502, the health service may be configured; i.e., initialized or set-up. For example, a recipient health model may be constructed, for example, as described in more detail elsewhere herein. Furthermore, in embodiments in which an MLE (e.g., the MLE 326) is used, the MLE may be pre-configured; e.g., trained or primed, for example, as described in more detail elsewhere herein. In some embodiments, the step 502 may include predefining one or more health communication characteristics, for example, any of the health communication characteristics described in relation to FIG. 4; and the health communication characteristics may be associated with one or more interventions and/or communications associated therewith.

In a step 504, a health device (e.g., the health device 200) of the recipient may be preconfigured before delivery of the health device to the recipient, for example, based at least in part on a recipient profile, which may include health information associated with the recipient; e.g., as described in more detail elsewhere herein.

In a step 506, operation of the health device may be managed. The step 506 may include authenticating a user of the health device as being an intended recipient/patient before activating the health device (i.e., enabling further use), for example, as described in more detail elsewhere herein. The step 506 also may include controlling power consumption and/or thermal output of the health device, as described in more detail elsewhere herein. It should be appreciated that the step 506 may be performed concurrently, at least in part, with other steps illustrated by the flow diagram 500.

In a step 508, health metric values of the recipient may be monitored, for example, by one or more health sensors, where the health metrics may be any of the health metrics described herein. For example, values of one or more health metrics may be detected continuously, or intermittently, e.g., periodically according to a set schedule or in response to user input. For example, a CGM may continuously detect glucose levels within a patient, or a blood pressure measurement using a blood pressure cuff may be used to detect blood pressure from a patient once a day or at the request of a physician.

In a step 510, other input associated with the recipient may be received. For example, the recipient may input text, audio, video or still images using input devices, for example, a keyboard, mouse, track ball, microphone, camera or other input device, including any of those described herein. In some embodiments, the other input may be input in response to a health communication. For example, the input may be a picture or video of a foot of a diabetes patient in response to an instruction included in a health communication from a health services application to photograph the foot of the patient. It should be appreciated that step 510 may be performed concurrently, at least in part, with the step 508.

In some embodiments, the other input received in the step 510 may include environmental or other contextual values, including, for example, time of day, whether it is daytime or nighttime; current temperature, whether a recipient is awake or asleep; whether the recipient is currently or was recently engaged in strenuous physical activity; when the recipient last ate; etc. Such environmental or other contextual values may be detected by a health device or entered into the health device by a recipient in connection with the health metric values being detected.

In a step 512, monitored values, and perhaps other input received at the health device, may be communicated to a health services application (e.g., the health services application 312) located remotely from the health device (e.g., on one or more servers), for example, using one or more of the network interface components described herein or by another means. In some embodiments, content input by a user may be converted from one media form (e.g., text or speech) in which it was received from the user to another media form (e.g., speech or text), and may be encoded in a different format than the format in which the content was received, for transmission to one or more servers on which a health services application resides. Converting the form of media or format of content input into the health device may be performed using audio logic and components described elsewhere herein.

In a step 513, the health data model 304, health treatment rules 306 and perhaps other data in the health services db(s) 302, and/or MLE parameters (e.g., weights of neural network layer or gates) may be updated based on the monitored health metric values(s) and/or other input received (e.g., actions performed) in the step 512. For example, the MLE may be configured to learn about the efficacy of actions performed in response to health communications. The learning may include comparing values of previous values of health metrics against values of such health metrics after actions prescribed by an intervention are taken. For example, the health services logic 320 (e.g., the MLE 326) may have produced a health communication 346 that specified multiple actions for a recipient (e.g., patient) 348 to take to reduce blood pressure. The recipient 348 may have undertaken the actions, which may be recorded in the step 522 and received as part of the other input (e.g., the action(s) performed 338) in the step 510. Furthermore, additional values of blood pressure metrics (e.g., included in health metrics 340) may have been received by the health device 344 in the step 508 since the actions were performed.

The recipient health models 304 and recipient data 303 of one or more recipients may be updated based on the actions(s) performed 338 in response to the health communication 346 and health metric values (e.g., blood pressure values) detected since the other actions were performed, as well as other raw recipient data 330 received from other health devices of other recipients and/or external health and patient db(s) 342 since the action were performed. The updating may include determining a proper chronology of events and measurements from difference sources, as described elsewhere herein.

The MLE 326 may analyze the effectiveness of the previously prescribed actions intended to treat a health condition (e.g., reduce blood pressure) by comparing the updated health metric values and other updated information to health metric values and other information received before the prescribed actions were performed. The parameters (e.g., weights) of the MLE 326 may be adjusted accordingly (in addition to determining interventions based on the updated information), either automatically and/or manually. An iterative performance of the foregoing over time should improve the accuracy of the MLE 326 in prescribing optimal interventions. It should be appreciated that step 513 may be performed at any time in relation to other steps of the method 500.

In a step 514, one or more interventions may be determined, for example, based on recipient health information, including detected health metric values, and/or one or more treatment rules. Determining interventions may include determining any of: whether it is necessary or desirable to perform one or more actions for the recipient; whether to communicate information (e.g., health information) to the recipient; the content of such information; and one or more characteristics of the communication of such information, as described in more detail elsewhere herein. One or more interventions may be determined autonomously and/or by human analysis, for example, as described in more detail elsewhere herein.

The step 514 may include determining that health metric values constitute an irregularity (e.g., an anomaly) with respect to previous health metric values detected from a recipient, for example, as described in more detail elsewhere herein. The step 514 additionally may include determining one or more interventions in response to detecting an irregularity, including, for example, sending communications to one or more entities (e.g., the recipient or a practitioner) as described in more detail elsewhere herein.

In a step 516, in response to determining one or more interventions, information may be communicated to the health device, for example, a part of a health communication, which may specify one or more actions corresponding to the determined one or more interventions. The health communication may be communicated to the health device according to health communication characteristics determined for the health communication in the step 514. In some embodiments, multiple health communications may be scheduled at different times based one the determinations made in the step 514.

In a step 518, in response to receiving information in the step 516, the health device may communicate information to the recipient, for example using a screen, speaker, visual indicator, and/or other output device of the health device. The information may specify one or more of the actions corresponding to the intervention(s), for example, in the form of a notification, instruction, inquiry, feedback request, and/or a portion of a live or automated conversation.

In a step 520, one or more actions corresponding to the one or more interventions, and specified in a health communication, may be performed, for example, by the recipient, the caregiver and/or the health device itself. It should be appreciated that the one or more actions corresponding to an intervention may range from very general and/or long-term actions to very specific, short-term actions. For example, such an action may include adjusting a care regimen or lifestyle, e.g., over a period of time; or taking a video or image of one or more parts of a patient's body, immediate surroundings, food, documents (e.g., paper prescriptions), medications, medication labels or other items. In embodiments in which images are taken, the method 520 may include applying recognition software to an image before or after the image is captured by a camera to determine whether the image is consistent with information in a health communication, and may be configured to reject the captured image and/or further instruct the recipient accordingly. For example, a message may be played or displayed to the user of the health device indicating rejection or acceptance of the images. The image recognition software may reside within and/or be executed by a controller (e.g., the controller 208) of the health device.

In a step 522, performance of one or more actions may be recorded. For example, the health device may detect that an action is performed and record performance of the action. Such action may include, for example, detecting blood pressure, taking a picture of a body part, taking a body temperature. The performance of other actions may be specified by user input and recorded. Such actions may include, for example: exercising, taking medication, observing a diet over a period of time. The foregoing detected and input actions may be included with received user input of the step 510, and included in the other input communicated to the health services application in the step 512. After performance of the step 522, control may return to the step 508, described above.

In addition to actions performed in accordance with an intervention, other actions may be recorded as well, such as, for example, the user of the health device opening and/or clicking on an email message, responding to a text or otherwise interacting with the health device.

It should be appreciated that performance of some or all of the steps of the flow diagram 500 may be performed iteratively, for example, as part of providing a real-time remote health service to a recipient. For example, such one or more steps may be performed such that information is exchanged at a rate at least similar to a rate at which information may be exchanged between a practitioner and recipient in an in-person meeting.

FIG. 6 is a flow diagram 600 illustrating constructing a health data model, according to embodiments of the system described herein. Other embodiments of constructing a health data model, for example, variations of processing illustrated by the flow diagram 600, are possible and are intended to fall within the scope of the invention.

In a step 602, recipient data may be aggregated from multiple potential sources. The recipient data may contain data described in more detail elsewhere herein, including the raw recipient data 330, which may include any of: the health history 332 of the recipient 348; the biographical data 334 about the recipient 348, the health metric values 340 of the recipient 348 detected by the health device 344; information concerning actions performed by the recipient 348 and/or the health device 344 (e.g., in response to one or more health communications 346 communicated by the health services application 312); and other information 336. The health history 332; the biographical info 334 and the other information 336 may be received from one or more health and/or recipient databases 342, which may be external databases controlled or maintained by other entities. Furthermore, the recipient data may include information gleaned from traditional "offline" data such as medical claims, pharmacy claims and medical lab results, and may include data that may influence health like geography, income, and ethnicity associated with the recipient. The data from the different data sources may be updated at different intervals, and may include imperfect identification information and other errors.

In a step 604, the aggregated recipient data may be reconciled to produce reconciled data (e.g., the reconciliation data 316). Reconciling the data may include normalizing recipient data into a similar data schema so that the recipient data; e.g., patient identification, time series, medical diagnoses, health metric values, performed actions and/or data measurement units, may be compared between data sources. Such reconciliation may include converting and formatting fields into canonical forms for accurate comparison, which may involve standardization of capitalization, punctuation, spacing, and numeric padding. Dates and times may be normalized to a single time zone for accurate comparison. Other data, for example, health metric values, may be converted to common units, e.g., metric vs. imperial. Reconciliation may further include identifying and matching recipients across different data sources using either exact matches on combinations of fields and/or using high-probability indirect matching. The fields may include, for example: name, birth date, insurance numbers, employee ID, phone number, or email address. Indirect identity matching between disparate data sets may rely on explicit matching logic. For example, "Bob" from one source may be the same name as "ROBERT" from another. The system also may leverage explicit language-specific name equivalencies. Matching also may be assisted by statistical correlations derived from large data sets. Other techniques for matching may be employed.

The reconciliation at the step 604 may include merging a chronology of data (e.g., health facts and interpretations) from the multiple data sources into a single merged absolute timeline.

In a step 606, a health model/profile (e.g., the health data model 304) may be built from the reconciled recipient data. The health model may model present and past health statuses of the recipient/patient. The health model and underlying data thereof (e.g., the recipient data 303) may be used by an MLE, a rules-based engine and/or a practitioner to determine interventions, as will be described in more detail elsewhere herein.

The processing illustrated by the flow diagram 600, including aggregating and reconciling of recipient information and generation of a patient health data model or the like, may be repeated periodically, for example, in accordance with a predefined schedule, and/or may be performed in response to an event, for example, a user instruction.

As described elsewhere herein, in some embodiments, an MLE may be used to determine interventions. FIG. 7 is a flow diagram 700 illustrating preconfiguring such an MLE, according to embodiments of the system described herein. Other mechanisms for preconfiguring an MLE, for example, variations of the processing illustrated by the flow diagram 700, are possible and are intended to fall within the scope of the invention.

In a step 702, one or more data elements may be selected from available health data, for example, data available in the health services db(s) 302, to serve as features of the MLE. That is, features deemed most relevant to determining an intervention for a health condition may be selected. For example, for a patient being treated for a form of diabetes, the following data elements may be used as features: age, gender, body mass index (BMI), average fasting blood glucose, percent of time blood glucose is within a target range, average blood pressure, and level of physical activity. The number of features may be considered the number of dimensions of the one or more data sets (e.g., recipient health profiles) to be analyzed.

In a step 704, clusters may be identified from selected features. For example, a clustering algorithm may be applied to determine clusters for each given feature from among a plurality of data sets (e.g., recipient health profiles). For example, clusters of individuals with similar blood glucose patterns could be identified using features including age, gender, and body mass index.

In a step 706, one or more features may be removed from the recipient data, for example, to reduce the number dimensions of data to consider in determining interventions. For example, analysis may reveal that the value of one or more features are not determinative enough of an intervention; i.e., a strong correlation cannot be drawn between a value of a feature and any potential intervention. For example, the features selected in the step 702 may have included the altitude of the residence of the recipient, but analysis may have revealed that the altitude of the residence did not have a strong correlation to any other features or potential interventions. Accordingly, the value of analyzing a feature may be outweighed by the benefits of removing the feature from the analysis to save resources (e.g., computational resources and memory).

In step 708, the MLE may be initialized. For example, initial weights may be set manually (perhaps randomly) for certain functional parameters of the MLE. For example, in an embodiment in which an artificial neural network (NN) is implemented by the MLE, initial weights may be manually set for various layers (e.g., input, output, hidden) or gates of the NN that receive data sets (e.g. vectors) of health information.

In step 710, the MLE may be trained by running several data sets (i.e., input vectors) of health metric values (e.g., test data) through the MLE and comparing results (e.g., the determined interventions) to correct interventions based on the test data. That is, the correct or proper intervention based on previous analysis of the data by experts may be compared to the intervention(s) (e.g., output value(s)) determined by the MLE using known mathematical techniques. The calculated difference between the intervention(s) determined by the MLE and the correct intervention(s) may be used to tune (e.g., automatically) one or more weights of the functional parameters of the MLE, thereby adjusting the function(s) performed by the MLE. Comparing interventions and adjusting weights may be executed iteratively until the accuracy of the MLE in determining intervention(s) is deemed adequate (e.g., according to the results of a loss function).

As described elsewhere herein (e.g., with respect to the step 504), providing a remote service according to embodiments of the system described herein may include configuring a mobile health device prior to delivering possession to a recipient. FIG. 8 is a flow diagram 800 illustrating configuring a mobile health device prior to delivering the mobile health device to a recipient, according to embodiments of the system described herein. Other embodiments of configuring a mobile health device prior to delivering the mobile health device to a recipient, for example, variations of the processing illustrated by the flow diagram 800, are possible and are intended to fall within the scope of the invention.

In a step 802, a profile of the recipient may be accessed. The profile may include health information about the recipient, and other information about the recipient that may be desirable or necessary for pre-configuring functionality of the mobile health device of the recipient, and/or that may be used in some embodiments to enable authentication of the mobile device upon delivery of the health device to the recipient. The profile may be created, maintained and/or accessed by a vendor of the health device or another entity in a contractual relationship with the vendor or the recipient, e.g., a health care or fitness organization or facility, or by multiple entities pursuant to a partnership agreement or the like.

The recipient information from which the profile may be generated may be from one or more data sources, which may be owned and/or controlled by another entity. For example, such information may be obtained from the external health and patient db(s) 342 or from the health services db(s) 302. Given the potentially sensitive nature of at least some of the information, particularly health information, about the recipient, certain security measures may be required and implemented as part of obtaining the recipient information, generating the profile and/or maintaining the profile. Some of these required security measures may be mandated by government regulations, e.g., HIPAA regulations.

The profile may be accessed, and perhaps generated, in response to a purchase or order of the health device by, or on behalf of, the recipient. For example, an ID and/or secure credentials of the recipient may be presented at a time of the order or purchase, which may be used to authorize access to the profile. The profile may specify one or more other devices and/or contact information (e.g., email address, phone number) at which to contact the recipient to perform multiple-factor (e.g., two-factor) authentication of the recipient as the user of the health device at a later time. That is, the other devices and/or contact information may be registered to the recipient. The other device and/or contact information may be provided at the time of purchasing or ordering the device, or may have been provided earlier.

In a step 804, one or more parameters of a health device (e.g., the health device 200 or the health device 231) may be defined based on information in the profile, and, in a step 806, the health device may be configured based on the one on more parameter values. For example, accessibility features of the health device may be customized based on information about the recipient's hearing, vision or other physical capabilities. Furthermore, one or more parameter values of a health sensor (e.g., CGM, blood pressure sensor, etc.) included in the health device may be set based on information about a health condition of the recipient for which the health device is intended to be used to service. Other parameters may be defined (e.g., customized) based on an employer, insurer or service provider (e.g., doctor, trainer, coach) determined from the recipient's profile. Such parameters may include, for example, the look-and-feel (e.g., branding) of the user interface, access controls, and pre-loaded applications and capabilities.

In some embodiments, the health device may be configured with identifying information about the recipient, which may be used to authenticate the recipient as the user of the health device after delivering of the health device to the recipient, as described below.

As described elsewhere herein (e.g., with respect to the step 506), managing operation of a health device may include authenticating a user of a mobile health device. FIG. 9 is a flow diagram 900 illustrating authenticating a user of a mobile health device, for example, prior to an initial use of the mobile health device by the user, according to embodiments of the system described herein. Other embodiments of authenticating a user of a mobile health device, for example, variations of the processing illustrated by the flow diagram 900, are possible and are intended to fall within the scope of the invention. The processing illustrated by the flow diagram 900 may be implemented using the authentication logic 288 of the controller 280 (e.g., the controller 208).

In a step 902, possession of the health device may be given to the recipient or caregiver. For example, the health device may be given to the recipient at the time of purchase or delivered to a residence or business of the recipient.

In a step 904, a first communication may be sent from the health device to a health services application (e.g., the health services application 312) or another remote entity responsible for authenticating the user of the health device. The first communication may be sent in response to the health device being powered on, or in response to another action by an operator of the health device. The health device may be configured to send the first communication in response to the action by the operator. The first communication may include information identifying the device (e.g., by a serial number), and may identify the device as belonging to the recipient, for example, by supplying an ID, PIN and/or other unique information or credentials of the recipient.

In a step 906, a second communication may be sent from the health services application (or other authenticating entity) to another device and/or contact of the recipient. The second communication may be sent in response to receiving the first communication. The information within the first communication identifying the health device and/or the owner of the health device may be used to access the recipient profile and determine the contact and/or other device information of the recipient, to which the second communication is directed. The second communication may include an access code (e.g., a one-time password (OTP)).

In a step 908, a third communication may be received at the health services application. In some embodiments, the third communication may be from the health device. In such embodiments, to determine whether the user device is authentic in a test step 910, it may be determined whether the third communication includes the access code transmitted in the second communication. If the access code in the third communication matches the access code included in the second communication, then, control transfers to a step 914 where the identity of the user of the health device as the recipient may be deemed authentic, and use of the health device allowed. For example, the health device may be activated in response to the authentication.

If it is determined in the step 910 that the access code in the third communication does not match the access code included in the second communication, then control transfers to a step 912 where the device may not be activated, i.e., use may not be allowed. That is, identity of the current user of the health device may be deemed inauthentic and use of the device by the current user rejected.

In some embodiments, the third communication may be received from the other device and/or contact of the recipient. In such embodiments, it may be determined in the step 910 whether the third communication was received from the other recipient device and/or other contact registered for the recipient with the health services application. The determination may be made by comparing the identity (e.g., serial number) of the source device or the identity of the sender (e.g., email address or phone number) to the identity of the other device and/or contact information of the recipient in the recipient profile of the recipient.

In embodiments in which the third communication is received from the other device and/or contact of the recipient, if it is determined in the step 910 that the third communication was indeed received from the other device and/or contact registered to the recipient, then, in the step 914, the identity of the user of the health device as the recipient may be deemed authentic, and use of the health device allowed. For example, the health device may be activated in response to the authentication. If it is determined in the step 910 that the third communication was not received from the other device registered to the recipient, then, in the step 912, the device may not be activated, i.e., use may not be allowed. That is, identity of the current user of the health device may be deemed inauthentic and use of the device by the current user rejected.

As described elsewhere herein (e.g., with respect to the step 506), managing operation of a health device may include activating a mobile health device in response to detecting motion of the mobile health device. FIG. 10 is a flow diagram 1000 illustrating activating a mobile health device in response to detecting motion of the mobile health device, according to embodiments of the system described herein. Other embodiments of activating a mobile health device in response to detecting motion of the mobile health device, for example, variations of the processing illustrated by the flow diagram 1000, are possible and are intended to fall within the scope of the invention. The processing illustrated by the flow diagram 1000 may be implemented using the power control logic 284 of the controller 280 (e.g., the controller 208) in combination with the one or more of the motion sensors 222.

Processing begins at a first step 1002 where it is determined whether a start of motion has been detected. For example, the motion control sensor 222 may detect motion of the health device 200 in one or more dimensions. If such motion has not been detected, then the step 1002 will be repeated until such a motion is detected. In some embodiments, in addition to or as an alternative to the polling reflected by the repeated performance of the step 1002, the detection of motion may be received as an event or interrupt.

If the start of motion is detected in the step 1002, then control transfers to a step 1004 where the motion may be recorded for a predetermined period of time, for example, for a period of time deemed sufficient to determine whether the motion may be indicative of an action about to be performed. That is, a health device or a component thereof (e.g., a health sensor) or accessory thereto may have one or more motion profiles associated therewith. Each motion profile may specify a pattern and duration of motion indicative of the imminent use of the health device, e.g., to detect one or more values of health metrics. For example, the motion of a blood pressure cuff at a certain trajectory after a long period of not moving at all may be deemed indicative of an imminent blood pressure measurement. In contrast, general motion of a glucose level reader of a mobile health device may not be deemed indicative of an imminent use of the mobile health device, which may be frequently in motion as the recipient walks, drives or rides.

In a test step 1006, it may be determined whether the recorded motion is indicative of an imminent action, for example, the taking of blood pressure with a blood pressure cuff. The determination may be made by comparing the recorded motion of the health device 200, a component thereof, or an accessory thereto, to one or more motion profiles of the health device 200, component or accessory. The profiles may be stored on the health device 200 (for example, in a memory on the health device 200, e.g., the memory of the controller 208) or on a remote one or more servers on which a health services application resides. The comparison may be performed on the health device 200 itself, which may require retrieving the one or more motion profiles if not already stored in memory, or may be performed on the one or more servers, in which case the recorded motion may be transmitted to the one or more servers to be compared.

If it is determined in the step 1006 that the recorded motion is not indicative of an imminent action, then control transfers to a step 1010, where it may be determined whether to continue recording motion. For example, it may be known (e.g., by the power control logic 284) from the one or more motion profiles associated with the device whether there are motion profiles of longer periods of time to which to compare recorded motion. If there are no such motion profiles, then control transfers to a step 1012 where recording is stopped. Following the step 1012, control may return to the step 1002, described above, to begin another iteration to detect a next start of motion.

If it is determined in the step 1010 to continue recording, then control transfers back to the step 1004, described above, where motion may continue to be recorded for a predetermined period of time following by the step 1006, described above, to determine if the recorded motion is indicative of an imminent action. That is, motion may be recorded for a longer and/or new period(s) of time, and then compared again to the one or more motion profiles.

If it is determined in the step 1006 that the recorded motion is indicative of an imminent action (e.g., a detecting of health metric values), then control transfers to a step 1008 where the health device, or one or more components thereof, may be activated (e.g., powered on and/or initialized). Activating the device or components thereof when action(s) are imminent may avoid delays in performing functions (e.g., detecting metric values, determining interventions, and other activities) that could be caused by trying to activate components while performance of these functions is initiated.

In some embodiments, the health device, or one or more components thereof, may be activated in response to detecting other actions, for example, the connecting of one or more accessories to the health device. For example, the health device or one or more components thereof may be powered on and/or initialized in response to detecting a blood pressure cuff being plugged into a plug (e.g., any of the plugs 218, 224, 250, 252, 268 and 270) or a test strip (e.g., the test strip 234) being inserted into a reader (e.g., the reader 230). Activating the device or components thereof in response to such actions may avoid delays in performing functions and other activities that could be caused by trying to activate components while performance of these functions is initiated.

As described elsewhere herein (e.g., with respect to the step 506), managing operation of a health device may include reducing thermal output of a mobile health device based on detected temperature. FIG. 11 is a flow diagram 1100 illustrating reducing thermal output of a mobile health device based on detected temperature, according to embodiments of the system described herein. Other embodiments of reducing thermal output of a mobile health device based on detected temperature, for example, variations of the processing illustrated by the flow diagram 1100, are possible and are intended to fall within the scope of the invention. The processing illustrated by the flow diagram 1100 may be implemented using the power control logic 284 of the controller 280 (e.g., the controller 208) in combination with the one or more temperature sensors 228.

In a step 1102, health metric values may be detected, for example, as described elsewhere herein. In a step 1104, in one or more regions of the health device, a respective temperature may be detected, for example, using the one or more temperature sensors 228 (e.g., thermometers, thermistors). In a step 1106, it may be determined whether the temperature is too high; i.e., whether the temperature has passed a predefined threshold. For example, the power control logic 284 may be configured to receive detected temperature values from the one or more temperature sensors 228 and compare the temperature values to threshold temperatures stored in a memory on the health device 200. The threshold temperatures may have been provided by the health services application 312 and may be updated from time to time, for example, if analysis reveals that one or more thresholds should be revised. Alternatively, the threshold temperatures may be maintained by the health services application, and retrieved therefrom for comparison by the power control logic 284; or the detected temperatures may be communicated to the health services application to be compared to the thresholds, and the results of the comparison communicated back to the power control logic 284.

If it is determined in the step 1106 that the temperature is too high, then control transfers to a step 1108 where one or more action(s) may be taken or continued (i.e., if the one or more action(s) were previously taken already when a too-high temperature was previously detected) to reduce the temperature; e.g., to reduce the thermal output of the health device or one or more components thereof. For example, in an embodiment in which the controller has multiple processing cores (e.g., CPU cores), one or more of the cores or CPUs thereof may be deactivated or not used to execute instructions. In some embodiments, the step 1106 may include decreasing a frequency of instruction execution of one or more processing cores or individual CPUs.

In a step 1110, the detected health metric values may be adjusted to accommodate that a temperature within one or more regions of the at the time of detection may have affected the accuracy of the values detected. Such adjustments may be made based on rules and/or information (e.g., stored within data structures on the controller 208 or within the health services db(s) 302), which may be based on empirical data from past observations.

In a step 1112, the health metric values may be processed, for example, as described in detail elsewhere herein, e.g., to be used to determine interventions. After performance of the step 1112, control returns to the step 1102, described above, to begin another iteration. It should be appreciated that performance of steps 1106, 1108 may include performing one or more actions during one iteration and one or more different actions during later iterations. For example, after a processing core is deactivated and/or an execution frequency of a core reduced during one pass, another processing core may be deactivated and another core's frequency reduced, or a core's execution frequency reduced further, during a later pass. Furthermore, the processing illustrated by the flow diagram 1100 may include re-activating cores and increasing execution frequencies of cores as temperatures decline.

Figure 12:
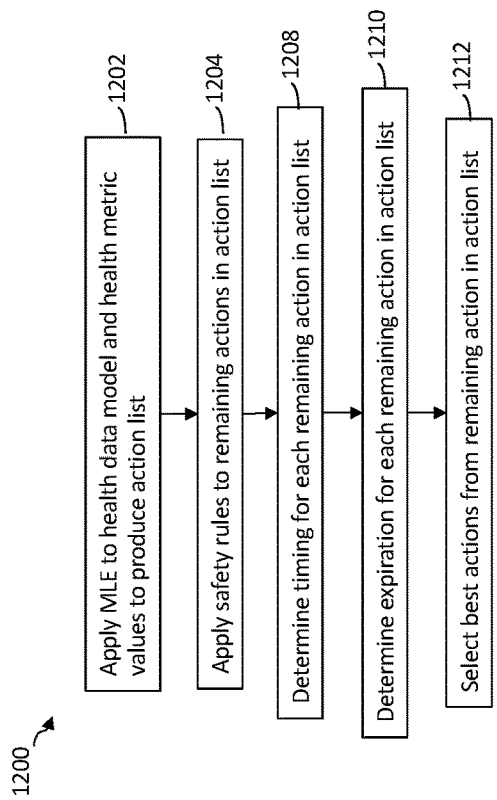
FIG. 12 is a flowchart illustrating applying an MLE to determine one or more interventions as part of providing a health service, according to embodiments of the system described herein.

As described elsewhere herein, an MLE may be applied to determine one or more interventions as part of providing a health service. FIG. 12 is a flow diagram 1200 illustrating applying an MLE to determine one or more interventions as part of providing a health service, according to embodiments of the system described herein. Other embodiments of applying an MLE to determine one or more interventions as part of providing a health service, for example, variations of the processing illustrated by the flow diagram 1200, are possible and are intended to fall within the scope of the invention. The processing illustrated by the flow diagram 1200 or portions thereof may be implemented using the MLE 326. Furthermore, it should be appreciated that one or more aspects of the processing illustrated by the flow diagram 1200 may be performed using a mechanism other than an MLE and techniques other than machine learning, for example, by applying rules-based logic such as, for example, the rules analysis logic 324.

In a step 1202, the MLE (e.g., the MLE 326) may be applied to a recipient health model (e.g., the health data model 304) and health metric values (e.g., the health metric values 340) to produce an action list (i.e., a list of intervention actions). In some embodiments, the health metric values have already been aggregated (and normalized as necessary) into the recipient health model such that the health metric values are not separately input to the MLE.

In some embodiments, an action list produced by the step 1202 is a ranked list; i.e., the step 1202 includes ranking the determined actions, e.g., based on which action is deemed optimal for treating whatever condition is being serviced; i.e., for producing an optimal health outcome. For example, the MLE may have been previously initialized and trained as described in more detail elsewhere herein, which may have involved using the health data model 304. The step 1202 may include applying the MLE after the training to produce a list of one or more actions. For each determined action, the MLE also may have calculated a value (e.g., a weight or score) indicative of the effectiveness of the action for the health condition being serviced, and the one or more actions may be ranked according to an effectiveness value.

In some embodiments, the step 1202 may include determining a sequence of two or more actions; i.e., two or more actions to be performed in a specific sequence. For example, the actions may include taking a first medicine before taking a second medicine. In such embodiments, the sequence of actions may be treated as a unit. For example, either all actions of the sequence performed in the order prescribed, or none of the actions are performed (e.g., are filtered out).

In a step 1204, safety rules may be applied to any remaining actions in the action list, for example, as described in more details elsewhere herein. As noted above, employing machine learning to autonomously or semi-autonomously determine interventions may be more dynamic and flexible than employing purely rules-based analysis, but the results also may be more unpredictable than those from rules-based analysis. Accordingly, for safety reasons, it may be desirable to use safety rules and/or a list of safe or unsafe actions to filter a list of actions. In some embodiments, the filtering may be applied before the step 1202; for example, to rule out the possibility of any potentially dangerous actions being produced from the step 1202.

Safety rules may include rules that require that certain conditions be met to perform an action and/or that prohibit performance of an action if certain conditions are met. For example, a rule might specify that a health communication of "Go exercise for at least 10 minutes" cannot be prescribed to a recipient if an average and/or most recently measured blood glucose level is below 60. Another rule may specify that a health communication instructing the user to take insulin cannot be communicated unless the medical record pf the recipient indicate that the recipient is insulin-dependent. Any of a variety of other safety rules may be defined and applied.

In a step 1208, timing for each remaining action in the action list may be determined; and in a step 1210, a respective expiration for each remaining action in the action list may be determined. For example, a determined action may be that a patient is directed to take a medication, but only if the medication is taken between 8:00 pm and 10:00 pm, an estimated time period approaching a bedtime of the patient. The action may have a timing of 8:00 pm and an expiration of 10:00. Thus, a health communication 346 may be sent at 8:00 pm, causing a message instructing the patient to take the medication to be displayed on a screen of the health device until 10:00 pm, at which time the message may stop being displayed.

In a step 1212, the best actions may be selected from any remaining actions in the action list. For example, as described elsewhere herein, the actions may be ranked based on a determined effectiveness of the actions (e.g., based on a determined effectiveness value). One or more top ranked action may be selected. For example, it may be determined that, even though there are several remaining actions in the list, the number of actions or the required instructions or explanations to send for the quantity of actions it too much to perform and/or digest, respectively, such that the list should be pared down. In such a case, it may be determined that a certain number of actions should be removed (e.g., from bottom of the ranked list), and the remaining actions communicated to the recipient. For example, a rule may be applied or configured into MLE logic to limit the number of interventions communicated to a recipient per day (e.g., one, two or three per day) and/or to certain times of day (e.g., only one intervention communicated before noon, and one communicated after 5:00 pm), perhaps with exceptions for urgent or emergency interventions.

As described elsewhere herein, determining an intervention may include determining a list of one or more actions to perform, and may include, as described with respect to the step 1204 of the flow diagram 1200, filtering the action list by applying safety rules to the list before or after other filtering is applied to the list; that is, safety rules may be applied to the remaining actions in a list of interventions. Applying safety rules to a list of intervention may include filtering the list of interventions against a list of safe actions.

Figure 13:
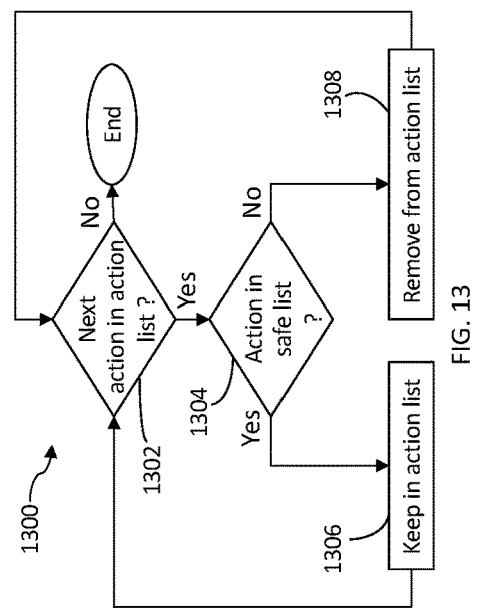
FIG. 13 is a flowchart illustrating filtering a list of one or more determined actions against a list of safe actions, according to embodiments of the system described herein.

FIG. 13 is a flow diagram 1300 illustrating filtering a list of one or more determined actions against a list of safe actions, according to embodiments of the system described herein. Other embodiments of filtering a list of one or more determined actions against a list of safe actions, for example, variations of the processing illustrated by the flow diagram 1300, are possible and are intended to fall within the scope of the invention.

In a step 1302, it may be determined whether there is a next (e.g., first) action in the ranked list. If it is determined in the step 1302 that there is not a next action in the ranked list (i.e., all actions in the action list have been processed), then processing is complete. Otherwise, control transfers to a step 1304 where it is determined whether a next action is in a safe list. The safe list may have been previously generated, e.g., manually by a practitioner, group of practitioners or organization, and may have been provided in an external source.

If it is determined in the act 1304 that the next action is in the safe list, then control transfers to a step 1306 where the next action is kept in the action list; otherwise, control transfers to a step 1308 where the next action is removed. Following either the step 1306 or the step 1308, control transfers back to the step 1302 for another iteration.

In some embodiments, in addition to, or as an alternative to, applying a safe list, the list of actions may be filtered against a list of unsafe (e.g., clinically unsafe) actions, which may involve applying similar (but converse) actions as described above with respect to a safe list of actions.

Figure 14:
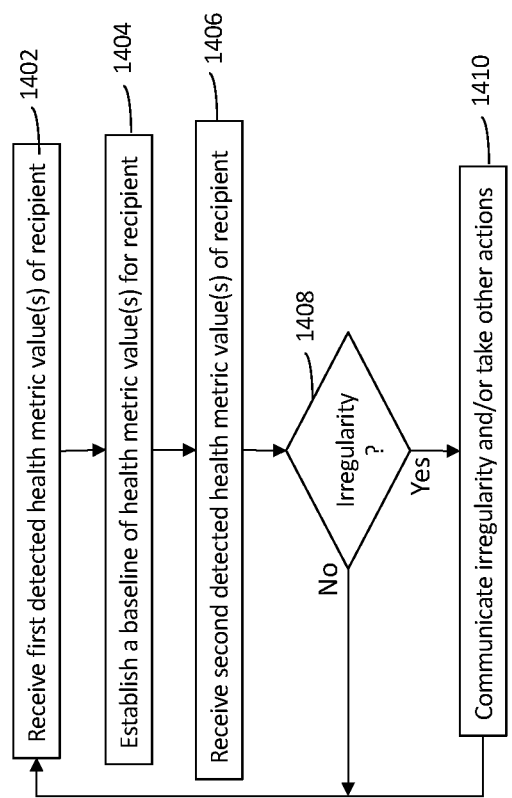
FIG. 14 is a flowchart illustrating detecting irregularities of health metric values, and taking action based on this detection, according to embodiments of the system described herein.

As described elsewhere herein (e.g., in connection with the step 514 of the flow diagram 500), determining interventions may include detecting irregularities of health metric values and determining one or more interventions based on detecting irregularities. FIG. 14 is a flow diagram 1400 illustrating detecting irregularities of health metric values, and taking action based on the detection, according to embodiments of the system described herein. Other embodiments of detecting irregularities of health metric values, and taking action based on the detection, for example, variations of the processing illustrated by the flow diagram 1400, are possible and are intended to fall within the scope of the invention. An irregularity may mean that: the person from whom health metric values were detected is not the recipient; one or more components of the health device are not working properly; and/or there has been a significant, perhaps dangerous, change in a health condition of the recipient.

In a step 1402, one or more first detected health metric values of a recipient may be detected. Such values may be detected during multiple performances of the step 508 as part of performance of the processing illustrated by the flow diagram 500. From the first detected metric values, a baseline for the health metric values (e.g., blood pressure, blood glucose levels, heart rate, weight, body mass index (BMI), cholesterol levels, triglyceride levels, etc.) may be established. The baseline values may be recorded as part of the recipient data 303 and/or the health data model 304.

In a step 1406, one or more second health metric values may be detected, for example, as part of a later performance of the step 508. In a step 1408, it may be determined whether any of the one or more second health metric values constitute an irregularity, for example, as part of performance of the step 514 of the processing illustrated by the flow diagram 500. For example, for one or more health metrics, the second values of the health metrics may be compared to the respective baseline values for the health metrics. If a calculated difference (e.g., an absolute or percentage difference) is above a certain threshold, it may be determined to constitute an irregularity. A calculated difference below a threshold may be interpreted to not constitute an irregularity. For example, a weight loss threshold of 20% over a predetermined period of time may be defined (e.g., in a rule) such that a loss of 20% or more (e.g., 40% body) of weight over the predetermined period of time may be deemed an irregularity, whereas a loss of less than 20% (e.g., 5%) may not be deemed an irregularity.

Determining an irregularity may involve considering factors other than the differences in health metric values, including, for example: the time period over which the values were detected; a rate of change over a time period; and context and conditions during which the values were detected (e.g., hot summer day; during or immediately after strenuous exercise or other activity; immediately following a meal; during daytime; while asleep). For example, a 40% increase in heartrate from a baseline heartrate may not be significant if detected immediately following a kick-boxing session, but may be considered an irregularity if detected while the recipient has been at rest for a certain period of time. These contextual values may be detected by a health device or entered into the health device by a recipient in connection with the health metric values being detected.

If it is determined in the step 1408 that there is an irregularity, then one or more actions to take may be determined (e.g., as part of performance of the step 514), and in a step 1410 the one or more actions may be taken. The one or more actions may include communicating the irregularity to one or more entities including, for example, the recipient (e.g., on the health device or to another device and/or contact for the recipient), the caregiver of the recipient; a practitioner; a healthcare organization; etc. Communicating the irregularity may alert the one or more entities to the possibilities that: someone other than the recipient is using the health device; the health device (e.g., one or more sensors thereof) is not working properly; there has been a significant, potentially dangerous, change in a health condition of the recipient. The communications of the irregularity may take any of a variety of forms, including any of the communication and/or media types described herein. For example, a visual and/or audial alarm (e.g., a blinking light, repeating beep) may be displayed or played, respectively, on the health device; and/or a high priority notification may be sent to a physician.

Various embodiments discussed herein may be combined with each other in appropriate combinations in connection with the system described herein. Additionally, in some instances, the order of steps in the flowcharts, flow diagrams and/or described flow processing may be modified, where appropriate. Furthermore, various aspects of the system described herein may be implemented using software, firmware, hardware, a combination of software, firmware and/or hardware and/or other computer-implemented modules or devices having the described features and performing the described functions.

Software implementations of the system described herein may include executable code that is stored on one or more computer readable media and executed by one or more processors. Each of the one or more computer readable media may be non-transitory and include a computer hard drive, ROM, RAM, flash memory, portable computer storage media such as a CD-ROM, a DVD-ROM, a flash drive, an SD card and/or other drive with, for example, a universal serial bus (USB) interface, and/or any other appropriate tangible or non-transitory computer readable medium or computer memory on which executable code may be stored and executed by a processor. The system described herein may be used in connection with any appropriate operating system.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c]. In addition, use of a an ordinal term, e.g., "first," "second" or the like, to qualify a term for an item having multiple instances of the same name does not necessarily indicated a priority, precedence or temporal order between the instances unless otherwise indicated, but rather such ordinal terms may be used merely to distinguish between the separate instances.

Other embodiments of the system described herein will be apparent to those skilled in the art from a consideration of the specification or practice of the system disclosed herein. It is intended that the specification and examples be considered as exemplary only, with the true scope and spirit of the invention being indicated by the following claims.

What is claimed is:

1. A mobile health device, comprising:
   a sensor that monitors values of a health metric of a person;
   a control component that controls the mobile health device to perform actions as part of providing a health service, wherein the control component includes an input that receives audio signals corresponding to the monitored values of the health metric, and produces a control signal based on information about the person, including the monitored values of the health metric of the person, wherein the control component converts each received audio signal to an input value and determines the control signal based on the input value; and
   components of the mobile health device that receive the control signal and perform an action to provide the health service based on the control signal, wherein the components include one or more user output components for producing sound and/or displaying information and wherein providing the health service includes one or more of: playing information as sound, displaying information as text, displaying information as motion video, and displaying information still images.

2. The mobile health device of claim 1, further comprising:
   a network interface component that communicates with a remote device that is remotely coupled to the mobile health device as part of providing the health service.

3. The mobile health device of claim 2, wherein the network interface component communicates the monitored values to the remote device, which has an audio capture device that captures voice signals corresponding to the monitored values of the health metric.

4. The mobile health device of claim 2, wherein the network interface component receives communications from the remote device that include encoded audio information corresponding to the provided health service the mobile health device further comprising: an audio player that produces decoded audio signals from the encoded audio information; and a speaker that produces sound from the decoded audio signals.

5. The mobile health device of claim 4, wherein the encoded audio information includes encoded voice signals of a health practitioner.

6. The mobile health device of claim 5, further comprising:
   an audio capture device that captures voice signals of the person;
   an audio encoding component that encodes the captured voice signals; and
   telephony logic communicatively coupled to the network interface component, the audio encoding component and the audio player that controls the exchange of real-time voice communications between the health professional and the person.

7. The mobile health device of claim 1, further comprising:
   an audio capture device that captures voice signals corresponding to the monitored values of the health metric from which the audio input signals are produced.

8. The mobile health device of claim 4, further comprising:
   a speech-to-text conversion module that converts voice signals to text associated with the health service, wherein the network interface component transmits information corresponding to the monitored values of the health metric based on the text.

9. The mobile health device of claim 1, wherein the health metric is a blood pressure level and/or blood glucose level.

10. For a mobile health device including a sensor that monitors values of a health metric of a person, a control component that controls the mobile health device to perform actions as part of providing a first health service, wherein the control component includes an input that receives audio signals corresponding to the monitored values of the health metric, and produces a control signal to control components of the mobile health device, and components that receive the control signal and perform an action based on the control signal as part of providing the health service, wherein the components include user output components that produce sound and/or display information, a method of operating the mobile health device, comprising:
   determining which of the following output actions to perform in providing the health service based on information about the person, including the monitored values of the health metric of the person:
     playing information as sound on the user output components,
     displaying information as text on the user output components,
     displaying information as motion video on the user output components, and
     displaying information as still images on the user output components; and
   the control component controlling the user output components to perform a determined user output action.

11. The method of claim 10, further comprising:
   a network interface component exchanging communications with a remote device that is remotely coupled to the mobile health device as part of providing the health service, wherein the network interface component receives communications from the remote device.

12. The method of claim 11, wherein the network interface component communicates the monitored values to the remote device, the remote device including an audio capture device that captures voice signals corresponding to the monitored values of the health metric from which the audio input signals are produced.

13. The method of claim 11, wherein network interface component receives communications from the remote device that include encoded audio information corresponding to the provided health service, and wherein the mobile health device further includes an audio player that produces decoded audio signals from the encoded audio information and includes a speaker that produces sound from the decoded audio signals.

14. The method of claim 13, wherein the encoded audio information includes encoded voice signals of a health practitioner.

15. The method of claim 14, further comprising:
   capturing voice signals of the person;
   encoding the captured voice signals, and
   exchanging real-time voice communications between the health practitioner and the person.

16. The method of claim 10, further comprising:
   capturing voice signals corresponding to monitored values of the health metric from which the first audio input signals are produced.

17. The method of claim 14, further comprising:
   converting voice signals to text associated with the provided first health service corresponding to the detected health metric; and
   transmitting information corresponding to the monitored values of the health metric based on the text.

18. The method of claim 10, wherein the health metric is a blood pressure level and/or blood glucose level.

19. For a mobile health device including a sensor that monitors values of a health metric of a person, a control component that controls the mobile health device to perform one or more actions as part of providing a health service, wherein the control component includes an input that receives first audio signals corresponding to monitored values of the health metric, and produces a control signal to control components of the mobile health device, and components that receive the control signal and perform an action based on the control signal as part of providing the health service, wherein the components include user output components for producing sound and/or displaying information, non-transitory computer-readable media having software stored thereon comprising:
   executable code that determines which one or more of the following output actions to perform to provide the health service based on information about the person, including the monitored values of the health metric of the person:
     playing information as sound on the user output components,
     displaying information as text on the user output components,
     displaying information as motion video on the user output components, and
     displaying information as still images on the user output components; and
   executable code within the control component that controls the user output components to perform the determined user output actions.

* * * * *